United States Patent
Lorenzo et al.

(10) Patent No.: US 11,890,020 B2
(45) Date of Patent: Feb. 6, 2024

(54) INTRASACCULAR ANEURYSM TREATMENT DEVICE WITH VARYING COATINGS

(71) Applicant: DePuy Synthes Products, Inc., Raynham, MA (US)

(72) Inventors: Juan Lorenzo, Raynham, MA (US); Lacey Gorochow, Miami, FL (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 723 days.

(21) Appl. No.: 17/031,709

(22) Filed: Sep. 24, 2020

(65) Prior Publication Data

US 2021/0007755 A1    Jan. 14, 2021

Related U.S. Application Data

(63) Continuation-in-part of application No. 16/997,543, filed on Aug. 19, 2020, now Pat. No. 11,672,543, and
(Continued)

(51) Int. Cl.
| | |
|---|---|
| *A61B 17/12* | (2006.01) |
| *A61B 90/00* | (2016.01) |
| *A61B 17/00* | (2006.01) |

(52) U.S. Cl.
CPC .... *A61B 17/12172* (2013.01); *A61B 17/1215* (2013.01); *A61B 17/12031* (2013.01);
(Continued)

(58) Field of Classification Search
CPC ........ A61B 17/12031; A61B 17/12113; A61B 17/12118; A61B 17/1214; A61B 17/1215;
(Continued)

(56) References Cited

U.S. PATENT DOCUMENTS

| | | | |
|---|---|---|---|
| 2,849,002 | A | 8/1958 | Oddo |
| 3,480,017 | A | 11/1969 | Shute |

(Continued)

FOREIGN PATENT DOCUMENTS

| | | |
|---|---|---|
| CA | 2395796 A1 | 7/2001 |
| CA | 2 431 594 A1 | 9/2002 |

(Continued)

OTHER PUBLICATIONS

Altes et al., Creation of Saccular Aneurysms in the Rabbit: A Model Suitable for Testing Endovascular Devices. AJR 2000; 174: 349-354.
(Continued)

*Primary Examiner* — Ryan J. Severson
(74) *Attorney, Agent, or Firm* — TROUTMAN PEPPER HAMILTON SANDERS LLP

(57) ABSTRACT

An aneurysm intrasaccular implant is provided having one or more coated regions. The implant includes a braided mesh movable from a delivery configuration having a single-layer tubular shape sized to traverse a catheter to an implanted configuration sized to be implanted in an aneurysm sac. The braided mesh can include an anti-thrombogenic coating defining a first section along the length of the braided mesh. The braided mesh can include a cell adhesion coating defining a second section along the length of the braided mesh. In the delivery confirmation, the first section can be positioned distal to the second section within the catheter. The second section is invertible to the implanted configuration such that the second section is positioned within the aneurysm sac and the first section is positioned to occlude an aneurysm neck.

20 Claims, 12 Drawing Sheets

Related U.S. Application Data a continuation of application No. 16/595,050, filed on Oct. 7, 2019, now abandoned, said application No. 16/997,543 is a continuation of application No. 15/903,860, filed on Feb. 23, 2018, now Pat. No. 10,751,066.

(60) Provisional application No. 62/462,685, filed on Feb. 23, 2017.

(52) U.S. Cl.
CPC .. *A61B 17/12113* (2013.01); *A61B 17/12118* (2013.01); *A61B 17/12168* (2013.01); *A61B 17/12177* (2013.01); *A61B 17/1214* (2013.01); *A61B 2017/00292* (2013.01); *A61B 2017/00867* (2013.01); *A61B 2017/1205* (2013.01); *A61B 2017/12054* (2013.01); *A61B 2017/12068* (2013.01); *A61B 2090/3966* (2016.02)

(58) Field of Classification Search
CPC ........ A61B 17/12168; A61B 17/12177; A61B 17/12172; A61B 2017/00292; A61B 2017/00867; A61B 2017/1205; A61B 2017/12054; A61B 2017/12068; A61B 2090/3966
See application file for complete search history.

(56) References Cited

U.S. PATENT DOCUMENTS

| | | |
|---|---|---|
| 4,085,757 A | 4/1978 | Pevsner |
| 4,282,875 A | 4/1981 | Serbinenko et al. |
| 4,364,392 A | 12/1982 | Strother et al. |
| 4,395,806 A | 8/1983 | Wonder et al. |
| 4,517,979 A | 5/1985 | Pecenka |
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,261,916 A | 11/1993 | Engelson |
| 5,304,195 A | 4/1994 | Twyford, Jr. et al. |
| 5,334,210 A | 8/1994 | Gianturco |
| 5,350,397 A | 9/1994 | Palermo |
| 5,423,829 A | 6/1995 | Pham et al. |
| 5,624,449 A | 4/1997 | Pham et al. |
| 5,645,558 A | 7/1997 | Horton |
| 5,733,294 A | 3/1998 | Forber et al. |
| 5,916,235 A | 6/1999 | Guglielmi |
| 5,891,128 A | 7/1999 | Yen et al. |
| 5,928,260 A | 7/1999 | Chin et al. |
| 5,935,148 A | 8/1999 | Villar |
| 5,941,249 A | 8/1999 | Maynard |
| 5,951,599 A | 9/1999 | McCrory |
| 5,964,797 A | 10/1999 | Ho |
| 6,007,573 A | 12/1999 | Wallace et al. |
| 6,024,756 A | 2/2000 | Pham |
| 6,036,720 A | 3/2000 | Abrams |
| 6,063,070 A | 5/2000 | Eder |
| 6,063,100 A | 5/2000 | Diaz et al. |
| 6,063,104 A | 5/2000 | Villar |
| 6,080,191 A | 6/2000 | Thaler |
| 6,086,577 A | 7/2000 | Ken et al. |
| 6,096,021 A | 8/2000 | Helm et al. |
| 6,113,609 A | 9/2000 | Adams |
| 6,123,714 A | 9/2000 | Gia et al. |
| 6,168,615 B1 | 1/2001 | Ken |
| 6,168,622 B1 | 1/2001 | Mazzocchi |
| 6,193,708 B1 | 2/2001 | Ken et al. |
| 6,221,086 B1 | 4/2001 | Forber |
| 6,270,515 B1 | 8/2001 | Linden et al. |
| 6,315,787 B1 | 11/2001 | Tsugita et al. |
| 6,331,184 B1 | 12/2001 | Abrams |
| 6,334,048 B1 | 12/2001 | Edvardsson et al. |
| 6,346,117 B1 | 2/2002 | Greenhalgh |
| 6,350,270 B1 | 2/2002 | Roue |
| 6,375,606 B1 | 4/2002 | Garbaldi et al. |
| 6,375,668 B1 | 4/2002 | Gifford |
| 6,379,329 B1 | 4/2002 | Naglreiter et al. |
| 6,391,037 B1 | 5/2002 | Greenhalgh |
| 6,419,686 B1 | 7/2002 | McLeod et al. |
| 6,428,558 B1 | 8/2002 | Jones |
| 6,454,780 B1 | 9/2002 | Wallace |
| 6,463,317 B1 | 10/2002 | Kucharczyk et al. |
| 6,506,204 B2 | 1/2003 | Mazzocchi |
| 6,527,919 B1 | 3/2003 | Roth |
| 6,547,804 B2 | 4/2003 | Porter et al. |
| 6,551,303 B1 | 4/2003 | Van Tassel et al. |
| 6,569,179 B2 | 5/2003 | Teoh |
| 6,569,190 B2 | 5/2003 | Whalen, II et al. |
| 6,572,628 B2 | 6/2003 | Dominguez |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lau et al. |
| 6,746,468 B1 | 6/2004 | Sepetka |
| 6,780,196 B2 | 8/2004 | Chin et al. |
| 6,802,851 B2 | 10/2004 | Jones |
| 6,811,560 B2 | 11/2004 | Jones |
| 6,833,003 B2 | 12/2004 | Jones et al. |
| 6,846,316 B2 | 1/2005 | Abrams |
| 6,849,081 B2 | 2/2005 | Sepetka et al. |
| 6,855,154 B2 | 2/2005 | Abdel-Gawwad |
| 6,949,116 B2 | 9/2005 | Solymar et al. |
| 6,964,657 B2 | 11/2005 | Cragg et al. |
| 6,964,671 B2 | 11/2005 | Cheng |
| 6,994,711 B2 | 2/2006 | Hieshima et al. |
| 7,044,134 B2 | 5/2006 | Khairkhahan et al. |
| 7,083,632 B2 | 8/2006 | Avellanet |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,153,323 B1 | 12/2006 | Teoh |
| 7,195,636 B2 | 3/2007 | Avellanet et al. |
| 7,229,454 B2 | 6/2007 | Tran et al. |
| 7,229,461 B2 | 6/2007 | Chin et al. |
| 7,309,345 B2 | 12/2007 | Wallace |
| 7,371,249 B2 | 5/2008 | Douk et al. |
| 7,377,932 B2 | 5/2008 | Mitelberg et al. |
| 7,410,482 B2 | 8/2008 | Murphy et al. |
| 7,572,288 B2 | 8/2009 | Cox |
| 7,597,704 B2 | 10/2009 | Frazier et al. |
| 7,608,088 B2 | 10/2009 | Jones |
| 7,695,488 B2 | 4/2010 | Berenstein et al. |
| 7,713,264 B2 | 5/2010 | Murphy |
| 7,744,652 B2 | 6/2010 | Morsi |
| 7,892,248 B2 | 2/2011 | Tran |
| 7,985,238 B2 | 7/2011 | Balgobin et al. |
| RE42,758 E | 9/2011 | Ken |
| 8,016,852 B2 | 9/2011 | Ho |
| 8,021,416 B2 | 9/2011 | Abrams |
| 8,025,668 B2 | 9/2011 | McCartney |
| 8,034,061 B2 | 10/2011 | Amplatz et al. |
| 8,048,145 B2 | 11/2011 | Evans et al. |
| 8,062,325 B2 | 11/2011 | Mitelberg et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,267,923 B2 | 9/2012 | Murphy |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand |

(56) References Cited

U.S. PATENT DOCUMENTS

| | | |
|---|---|---|
| 8,454,633 B2 | 6/2013 | Amplatz et al. |
| 8,523,897 B2 | 9/2013 | van der Burg et al. |
| 8,523,902 B2 | 9/2013 | Heaven et al. |
| 8,551,132 B2 | 10/2013 | Eskridge et al. |
| 8,777,974 B2 | 7/2014 | Amplatz et al. |
| 8,900,304 B1 | 12/2014 | Alobaid |
| 8,992,568 B2 | 3/2015 | Duggal et al. |
| 8,998,947 B2 | 3/2015 | Aboytes et al. |
| 8,974,512 B2 | 4/2015 | Aboytes et al. |
| 9,055,948 B2 | 6/2015 | Jaeger et al. |
| 9,107,670 B2 | 8/2015 | Hannes et al. |
| 9,161,758 B2 | 10/2015 | Figulla et al. |
| 9,232,992 B2 | 1/2016 | Heidner et al. |
| 9,259,337 B2 | 2/2016 | Cox et al. |
| 9,314,326 B2 | 4/2016 | Wallace et al. |
| 9,351,715 B2 | 5/2016 | Mach |
| 9,414,842 B2 | 8/2016 | Glimsdale et al. |
| 9,526,813 B2 | 12/2016 | Cohn et al. |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Bowman |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,096 B2 | 2/2017 | Kim et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,585,669 B2 | 3/2017 | Becking et al. |
| 9,615,832 B2 | 4/2017 | Bose et al. |
| 9,615,951 B2 | 4/2017 | Bennett et al. |
| 9,622,753 B2 | 4/2017 | Cox |
| 9,629,635 B2 | 4/2017 | Hewitt et al. |
| 9,636,115 B2 | 5/2017 | Henry et al. |
| 9,636,439 B2 | 5/2017 | Chu et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,681,861 B2 | 6/2017 | Heisel et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Paterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,826,980 B2 | 11/2017 | Figulla et al. |
| 9,833,252 B2 | 12/2017 | Sepetka et al. |
| 9,833,604 B2 | 12/2017 | Lam et al. |
| 9,833,625 B2 | 12/2017 | Waldhauser et al. |
| 9,918,720 B2 | 3/2018 | Marchand et al. |
| 9,955,976 B2 | 5/2018 | Hewitt et al. |
| 10,004,510 B2 | 6/2018 | Gerberding |
| 10,130,372 B2 | 11/2018 | Griffin |
| 10,307,148 B2 | 6/2019 | Heisel et al. |
| 10,327,781 B2 | 6/2019 | Divino et al. |
| 10,342,546 B2 | 7/2019 | Sepetka et al. |
| 10,517,604 B2 | 12/2019 | Bowman et al. |
| 10,653,425 B1 | 5/2020 | Gorochow et al. |
| 10,716,573 B2 | 7/2020 | Connor |
| 10,743,884 B2 | 8/2020 | Lorenzo |
| 10,751,066 B2 | 8/2020 | Lorenzo |
| 11,464,518 B2 | 10/2022 | Connor |
| 2002/0068974 A1 | 6/2002 | Kuslich et al. |
| 2002/0082638 A1 | 6/2002 | Porter et al. |
| 2002/0143349 A1 | 10/2002 | Gifford, III et al. |
| 2002/0147497 A1 | 10/2002 | Belef et al. |
| 2002/0188314 A1 | 12/2002 | Anderson et al. |
| 2003/0028209 A1 | 2/2003 | Teoh et al. |
| 2003/0120337 A1 | 6/2003 | Van Tassel et al. |
| 2003/0171739 A1 | 9/2003 | Murphy |
| 2003/0176884 A1 | 9/2003 | Berrada et al. |
| 2003/0181927 A1 | 9/2003 | Wallace |
| 2003/0181945 A1 | 9/2003 | Opolski |
| 2003/0195553 A1 | 10/2003 | Wallace |
| 2003/0216772 A1 | 11/2003 | Konya |
| 2004/0034366 A1 | 2/2004 | van der Burg et al. |
| 2004/0034386 A1 | 2/2004 | Fulton et al. |
| 2004/0044391 A1 | 3/2004 | Porter |
| 2004/0087998 A1 | 5/2004 | Lee et al. |
| 2004/0093014 A1 | 5/2004 | Ho et al. |
| 2004/0098027 A1 | 5/2004 | Teoh et al. |
| 2004/0127935 A1 | 7/2004 | Robert et al. |
| 2004/0133222 A1 | 7/2004 | Tran et al. |
| 2004/0153120 A1 | 8/2004 | Seifert et al. |
| 2004/0210297 A1 | 10/2004 | Lin et al. |
| 2004/0254594 A1 | 12/2004 | Alfaro |
| 2005/0021016 A1 | 1/2005 | Malecki et al. |
| 2005/0021072 A1 | 1/2005 | Wallace |
| 2005/0159771 A1 | 7/2005 | Petersen |
| 2005/0177103 A1 | 8/2005 | Hunter et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1 | 3/2006 | Gutterman et al. |
| 2006/0106421 A1 | 5/2006 | Teoh |
| 2006/0155323 A1 | 7/2006 | Porter et al. |
| 2006/0155367 A1 | 7/2006 | Hines |
| 2006/0167494 A1 | 7/2006 | Suddaby |
| 2006/0247572 A1 | 11/2006 | McCartney |
| 2007/0088387 A1 | 4/2007 | Eskridge et al. |
| 2007/0106311 A1 | 5/2007 | Wallace et al. |
| 2007/0208376 A1 | 6/2007 | Meng |
| 2007/0162071 A1 | 7/2007 | Burkett et al. |
| 2007/0167876 A1 | 7/2007 | Euteneuer et al. |
| 2007/0173928 A1 | 7/2007 | Morsi |
| 2007/0186933 A1 | 8/2007 | Domingo |
| 2007/0191884 A1 | 8/2007 | Eskridge et al. |
| 2007/0233188 A1 | 10/2007 | Hunt et al. |
| 2007/0265656 A1 | 11/2007 | Amplatz et al. |
| 2007/0288083 A1 | 12/2007 | Hines |
| 2008/0097495 A1 | 4/2008 | Feller, III et al. |
| 2008/0103505 A1 | 5/2008 | Fransen |
| 2008/0119886 A1 | 5/2008 | Greenhalgh et al. |
| 2008/0281302 A1 | 11/2008 | Murphy et al. |
| 2008/0281350 A1 | 11/2008 | Sepetka et al. |
| 2009/0036877 A1 | 2/2009 | Nardone et al. |
| 2009/0062841 A1 | 3/2009 | Amplatz et al. |
| 2009/0099647 A1 | 4/2009 | Glimsdale |
| 2009/0227983 A1 | 9/2009 | Griffin et al. |
| 2009/0281557 A1 | 11/2009 | Sander et al. |
| 2009/0287291 A1 | 11/2009 | Becking et al. |
| 2009/0287294 A1 | 11/2009 | Rosqueta et al. |
| 2009/0287297 A1 | 11/2009 | Cox |
| 2009/0318941 A1 | 12/2009 | Sepetka |
| 2010/0023046 A1 | 1/2010 | Heidner et al. |
| 2010/0023048 A1 | 1/2010 | Mach |

(56) References Cited

U.S. PATENT DOCUMENTS

| | | |
|---|---|---|
| 2010/0063573 A1 | 3/2010 | Hijlkema |
| 2010/0063582 A1 | 3/2010 | Rudakov |
| 2010/0069948 A1 | 3/2010 | Veznedaroglu et al. |
| 2010/0168781 A1 | 7/2010 | Berenstein |
| 2010/0211156 A1 | 8/2010 | Linder et al. |
| 2010/0324649 A1 | 12/2010 | Mattsson et al. |
| 2011/0046658 A1 | 2/2011 | Conner et al. |
| 2011/0054519 A1 | 3/2011 | Neuss |
| 2011/0112588 A1 | 5/2011 | Linderman et al. |
| 2011/0137317 A1 | 6/2011 | O'Halloran et al. |
| 2011/0152993 A1 | 6/2011 | Marchand et al. |
| 2011/0196413 A1 | 8/2011 | Wallace |
| 2011/0319978 A1 | 12/2011 | Schaffer |
| 2012/0010644 A1 | 1/2012 | Sideris et al. |
| 2012/0071911 A1 | 3/2012 | Sadasivan |
| 2012/0165732 A1 | 6/2012 | Müller |
| 2012/0191123 A1 | 7/2012 | Brister et al. |
| 2012/0283768 A1 | 11/2012 | Cox et al. |
| 2012/0310270 A1 | 12/2012 | Murphy |
| 2012/0323267 A1 | 12/2012 | Ren |
| 2012/0330341 A1 | 12/2012 | Becking et al. |
| 2013/0035665 A1 | 2/2013 | Chu |
| 2013/0035712 A1 | 2/2013 | Theobald et al. |
| 2013/0066357 A1 | 3/2013 | Aboytes et al. |
| 2013/0079864 A1 | 3/2013 | Boden |
| 2013/0110066 A1 | 5/2013 | Sharma et al. |
| 2013/0204351 A1 | 8/2013 | Cox et al. |
| 2013/0211495 A1 | 8/2013 | Halden et al. |
| 2013/0261658 A1 | 10/2013 | Lorenzo et al. |
| 2013/0261730 A1 | 10/2013 | Bose et al. |
| 2013/0274863 A1 | 10/2013 | Cox et al. |
| 2013/0345738 A1 | 12/2013 | Eskridge |
| 2014/0005714 A1 | 1/2014 | Quick et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0135812 A1 | 5/2014 | Divino et al. |
| 2014/0200607 A1 | 7/2014 | Sepetka et al. |
| 2014/0257360 A1 | 9/2014 | Keillor |
| 2014/0257361 A1 | 9/2014 | Prom |
| 2014/0277013 A1 | 9/2014 | Sepetka et al. |
| 2014/0358178 A1 | 12/2014 | Hewitt et al. |
| 2015/0057703 A1 | 2/2015 | Ryan et al. |
| 2015/0209050 A1 | 7/2015 | Aboytes et al. |
| 2015/0272589 A1 | 10/2015 | Lorenzo |
| 2015/0313605 A1 | 11/2015 | Griffin |
| 2015/0342613 A1 | 12/2015 | Aboytes et al. |
| 2015/0374483 A1 | 12/2015 | Janardhan et al. |
| 2016/0022445 A1 | 1/2016 | Ruvalcaba et al. |
| 2016/0030050 A1 | 2/2016 | Franano et al. |
| 2016/0192912 A1 | 7/2016 | Kassab et al. |
| 2016/0249934 A1 | 9/2016 | Hewitt et al. |
| 2016/0249935 A1 | 9/2016 | Hewitt et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079661 A1 | 3/2017 | Bardsley et al. |
| 2017/0079662 A1 | 3/2017 | Rhee et al. |
| 2017/0079671 A1 | 3/2017 | Morero et al. |
| 2017/0079680 A1 | 3/2017 | Bowman |
| 2017/0079717 A1 | 3/2017 | Walsh et al. |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0113023 A1 | 4/2017 | Steingisser et al. |
| 2017/0114350 A1 | 4/2017 | dos Santos et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0258473 A1 | 9/2017 | Plaza et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340333 A1 | 11/2017 | Badruddin et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0140305 A1 | 5/2018 | Connor |
| 2018/0206850 A1 | 7/2018 | Wang et al. |
| 2018/0242979 A1 | 8/2018 | Lorenzo |
| 2018/0303531 A1 | 10/2018 | Sanders et al. |
| 2018/0338767 A1 | 11/2018 | Dasnurkar et al. |
| 2019/0008522 A1 | 1/2019 | Lorenzo |
| 2019/0223878 A1 | 1/2019 | Lorenzo et al. |
| 2019/0110796 A1 | 4/2019 | Jayaraman |
| 2019/0142567 A1 | 5/2019 | Janardhan et al. |
| 2019/0192162 A1 | 6/2019 | Lorenzo |
| 2019/0192167 A1 | 6/2019 | Lorenzo |
| 2019/0192168 A1 | 6/2019 | Lorenzo |
| 2019/0223879 A1 | 7/2019 | Jayaraman |
| 2019/0223881 A1 | 9/2019 | Hewitt et al. |
| 2019/0328398 A1 | 10/2019 | Lorenzo |
| 2019/0357914 A1 | 11/2019 | Gorochow et al. |
| 2019/0365385 A1 | 12/2019 | Gorochow et al. |
| 2020/0000477 A1 | 1/2020 | Nita et al. |
| 2020/0069313 A1 | 3/2020 | Xu et al. |
| 2020/0268365 A1 | 8/2020 | Hebert et al. |

(56) References Cited

U.S. PATENT DOCUMENTS

| | | | |
|---|---|---|---|
| 2020/0367897 A1 | 11/2020 | Wolfe et al. | |
| 2020/0375606 A1 | 12/2020 | Lorenzo | |
| 2021/0007755 A1 | 1/2021 | Lorenzo et al. | |
| 2021/0177429 A1 | 6/2021 | Lorenzo | |

FOREIGN PATENT DOCUMENTS

| | | |
|---|---|---|
| CA | 2598048 A1 | 5/2008 |
| CN | 204 683 687 U | 7/2015 |
| CN | 107374688 A | 11/2017 |
| DE | 102008015781 A1 | 10/2009 |
| DE | 102010053111 A1 | 6/2012 |
| DE | 102009058132 B4 | 7/2014 |
| DE | 102013106031 A1 | 12/2014 |
| DE | 202008018523 U1 | 4/2015 |
| DE | 102011102955 B4 | 5/2018 |
| EP | 902704 B1 | 3/1999 |
| EP | 1054635 B1 | 11/2000 |
| EP | 1295563 A1 | 3/2003 |
| EP | 1441649 B1 | 8/2004 |
| EP | 1483009 B1 | 12/2004 |
| EP | 1527753 B1 | 5/2005 |
| EP | 1569565 B1 | 9/2005 |
| EP | 1574169 B1 | 9/2005 |
| EP | 1494619 B1 | 1/2006 |
| EP | 1633275 B1 | 3/2006 |
| EP | 1659988 B1 | 5/2006 |
| EP | 1725185 B1 | 11/2006 |
| EP | 1862122 A1 | 12/2007 |
| EP | 1923005 B1 | 5/2008 |
| EP | 2063791 B1 | 6/2009 |
| EP | 2134263 B1 | 12/2009 |
| EP | 2157937 B1 | 3/2010 |
| EP | 2266456 A1 | 12/2010 |
| EP | 2324775 B1 | 5/2011 |
| EP | 2367482 B1 | 9/2011 |
| EP | 2387951 B1 | 11/2011 |
| EP | 2460476 A2 | 6/2012 |
| EP | 2468349 A1 | 6/2012 |
| EP | 2543345 A1 | 1/2013 |
| EP | 2567663 A1 | 3/2013 |
| EP | 2617386 A1 | 7/2013 |
| EP | 2623039 A1 | 8/2013 |
| EP | 2647343 A2 | 10/2013 |
| EP | 2848211 A1 | 3/2015 |
| EP | 2854704 B1 | 4/2015 |
| EP | 2923674 B1 | 9/2015 |
| EP | 2926744 A1 | 10/2015 |
| EP | 3146916 A1 | 3/2017 |
| EP | 3501429 A1 | 6/2019 |
| EP | 3517055 A1 | 7/2019 |
| EP | 3 636 173 A2 | 10/2019 |
| EP | 3 636 171 A1 | 4/2020 |
| JP | H04-47415 U | 4/1992 |
| JP | H07-37200 U | 7/1995 |
| JP | 2006-509578 A | 3/2006 |
| JP | 2013-509972 A | 3/2013 |
| JP | 2013537069 A | 9/2013 |
| JP | 2014-522268 A | 9/2014 |
| JP | 2016-502925 A | 2/2015 |
| JP | 2016-518155 A | 6/2016 |
| WO | WO 9641589 A1 | 12/1996 |
| WO | WO 9905977 A1 | 2/1999 |
| WO | WO 9908607 A1 | 2/1999 |
| WO | WO 9930640 A1 | 6/1999 |
| WO | WO 2003073961 A1 | 9/2003 |
| WO | WO 03/086240 A1 | 10/2003 |
| WO | WO 2005020822 A1 | 3/2005 |
| WO | WO 2005074814 A2 | 8/2005 |
| WO | WO 2005117718 A1 | 12/2005 |
| WO | WO 2006034149 A2 | 3/2006 |
| WO | WO 2006052322 A2 | 5/2006 |
| WO | WO 2007076480 A2 | 7/2007 |
| WO | WO 2008150346 A1 | 12/2008 |
| WO | WO 2008151204 A1 | 12/2008 |
| WO | WO 2009048700 A1 | 4/2009 |
| WO | WO 2009105365 A1 | 8/2009 |
| WO | WO 2009132045 A2 | 10/2009 |
| WO | WO 2009135166 A2 | 11/2009 |
| WO | WO 2010030991 A1 | 3/2010 |
| WO | WO 2011057002 A2 | 5/2011 |
| WO | WO 2012032030 A1 | 3/2012 |
| WO | WO 2012099704 A2 | 7/2012 |
| WO | WO 2012099909 A2 | 7/2012 |
| WO | WO 2012113554 A1 | 8/2012 |
| WO | WO 2013016618 A2 | 1/2013 |
| WO | WO 2013025711 A1 | 2/2013 |
| WO | WO 2013109309 A1 | 7/2013 |
| WO | WO 2013159065 A1 | 10/2013 |
| WO | WO 2013162817 A1 | 10/2013 |
| WO | WO 2014029835 A1 | 2/2014 |
| WO | WO 2014078286 A1 | 5/2014 |
| WO | WO 2014110589 A1 | 7/2014 |
| WO | WO 2014137467 A1 | 9/2014 |
| WO | WO 2015073704 A1 | 5/2015 |
| WO | WO 2015160721 A1 | 10/2015 |
| WO | WO 2015166013 A1 | 11/2015 |
| WO | WO 2015171268 A2 | 11/2015 |
| WO | WO 2015184075 A1 | 12/2015 |
| WO | WO 2015187196 A1 | 12/2015 |
| WO | WO 2016044647 A2 | 3/2016 |
| WO | WO 2016107357 A1 | 7/2016 |
| WO | WO 2016137997 A1 | 9/2016 |
| WO | WO 2017/161283 A1 | 9/2017 |
| WO | WO 2018051187 A1 | 3/2018 |
| WO | WO 2019/038293 A1 | 2/2019 |
| WO | WO 2012/034135 A1 | 3/2021 |

OTHER PUBLICATIONS

Schaffer, Advanced Materials & Processes, Oct. 2002, pp. 51-54.

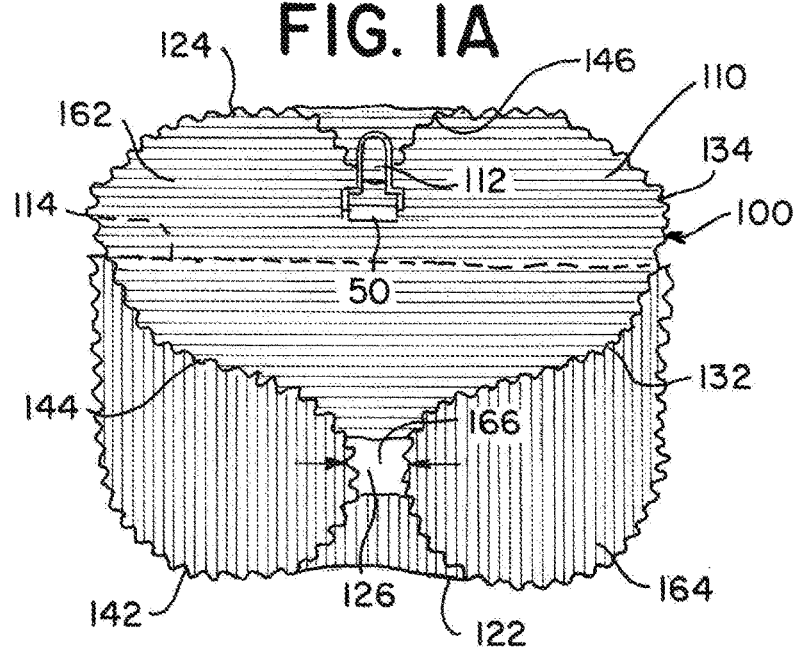
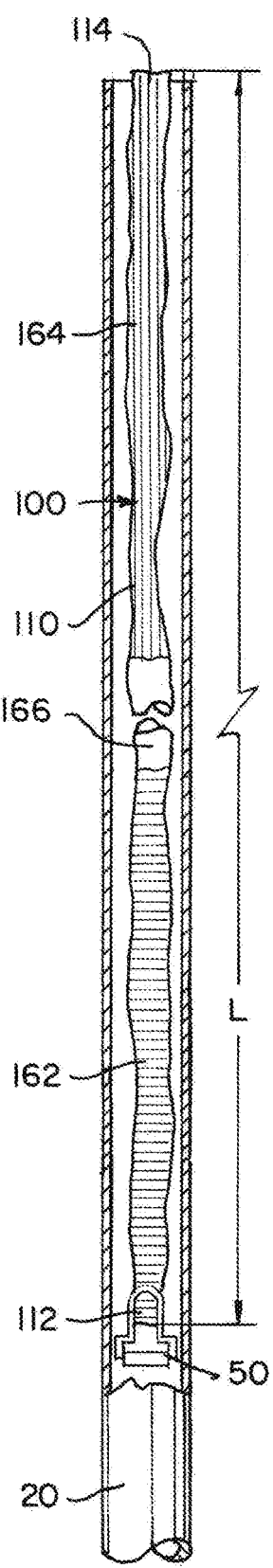
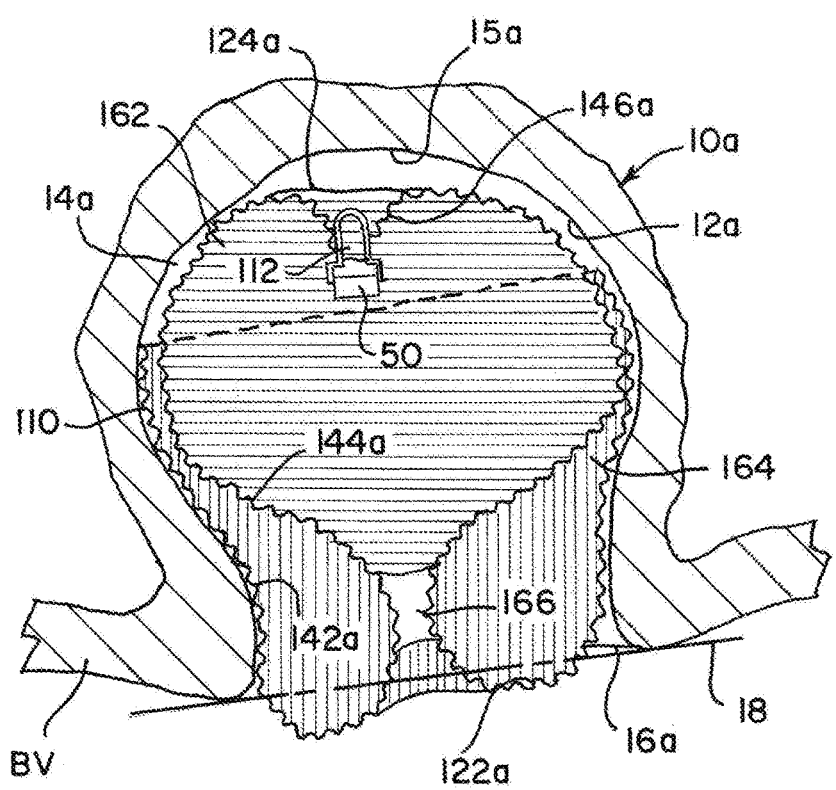

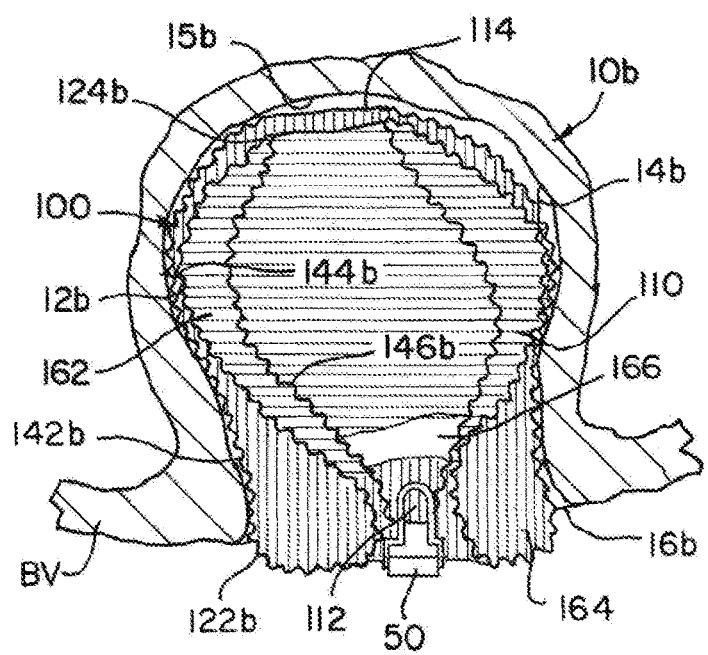

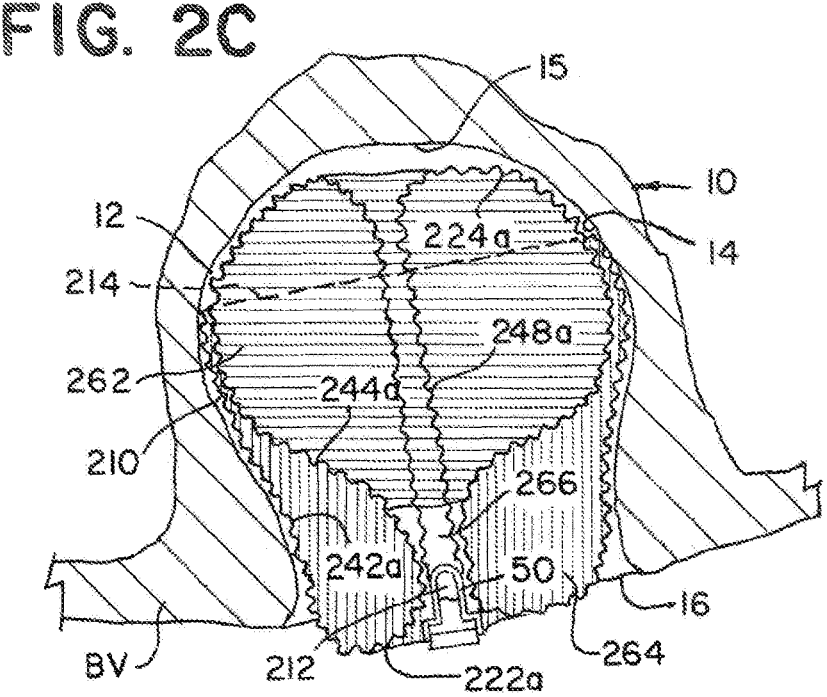

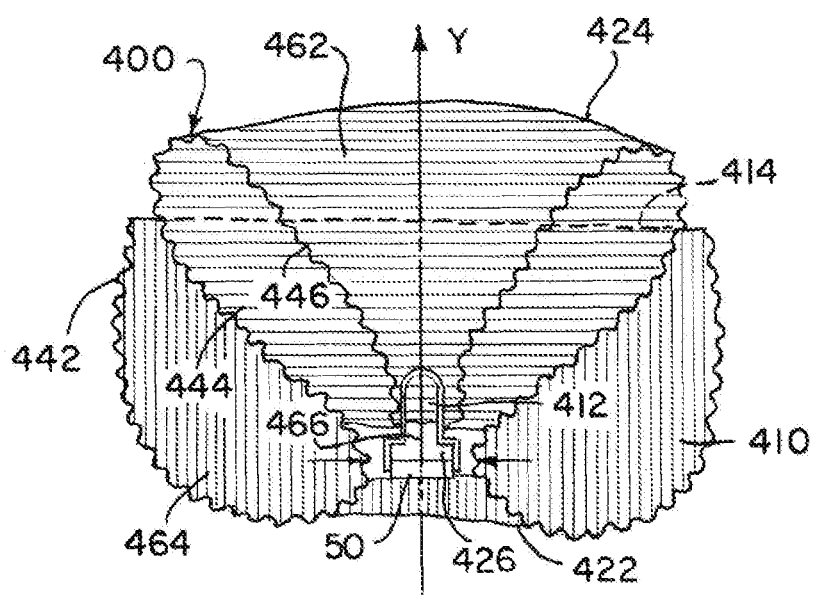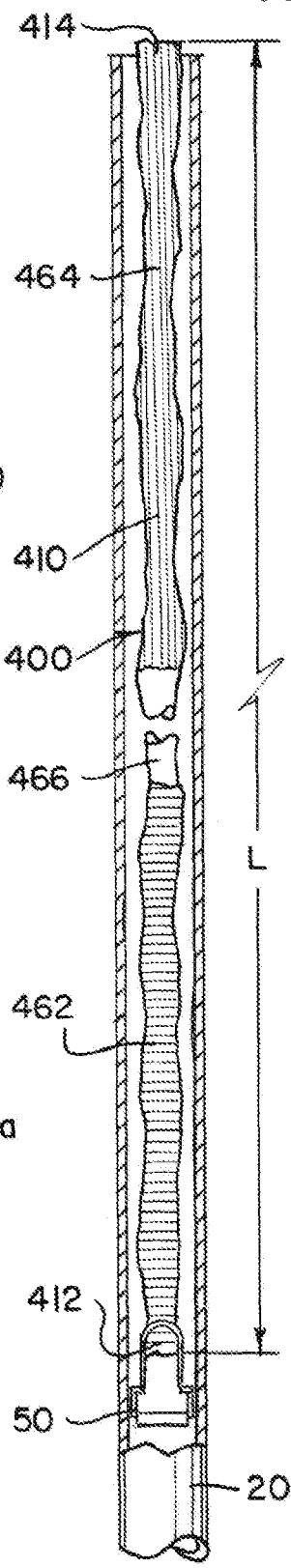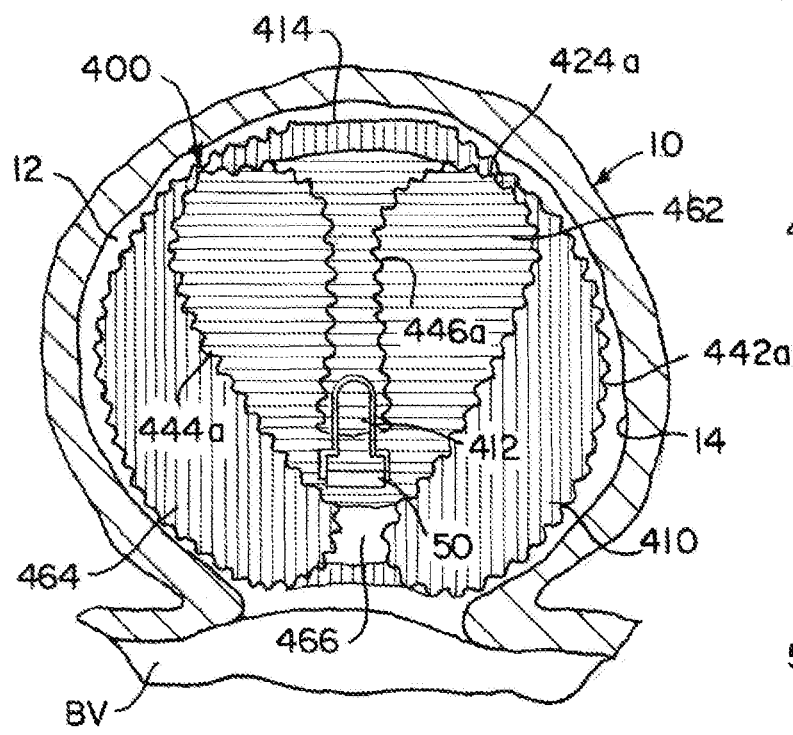

FIG. 5A
FIG. 5B
FIG. 5C
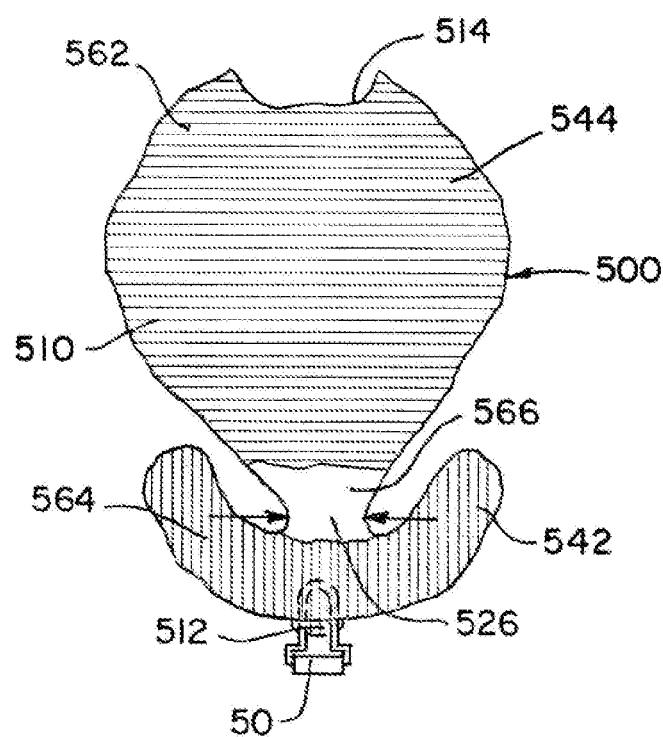
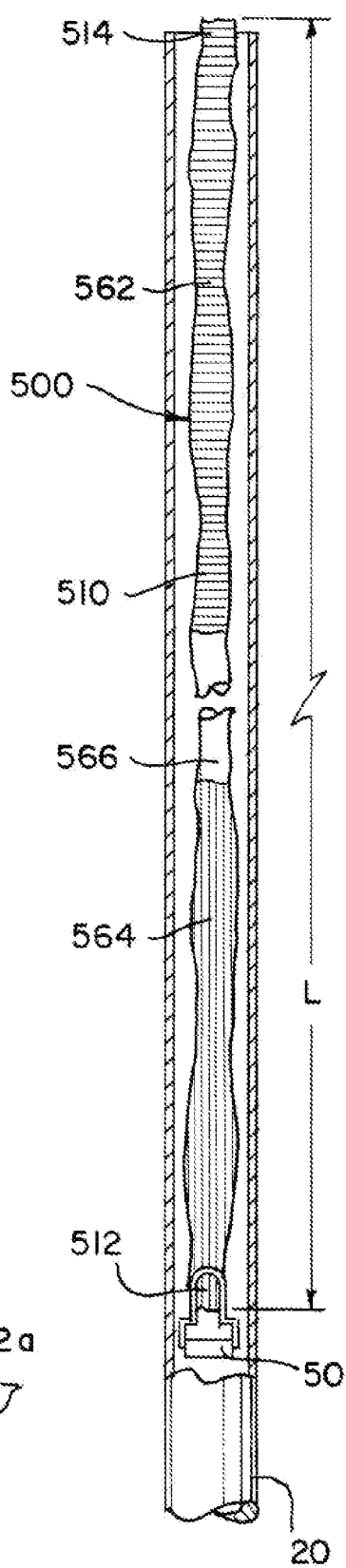
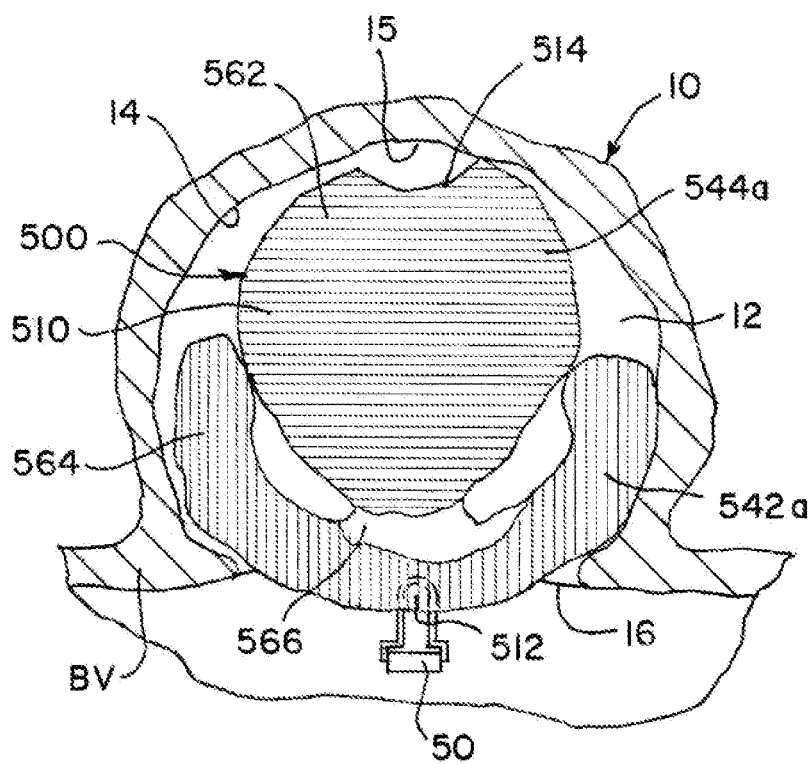

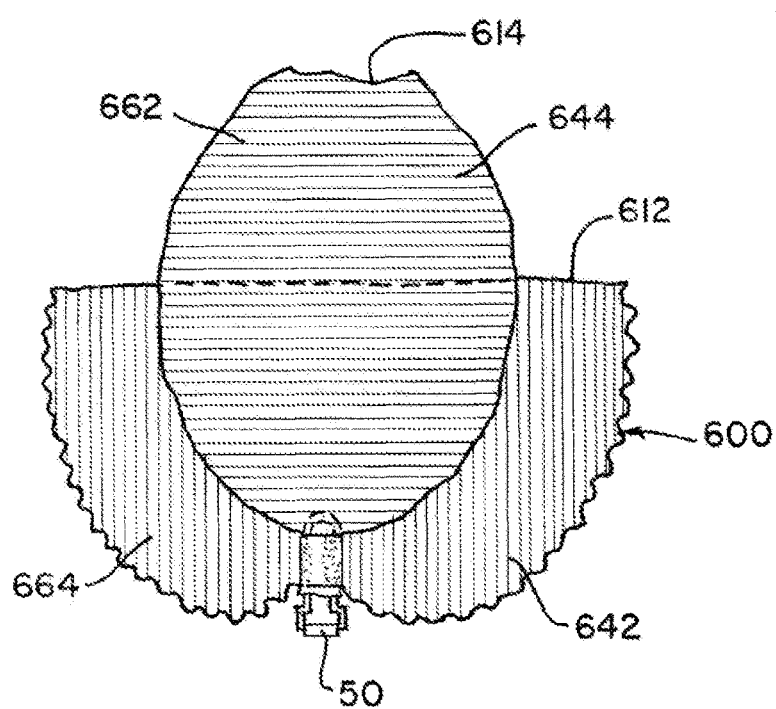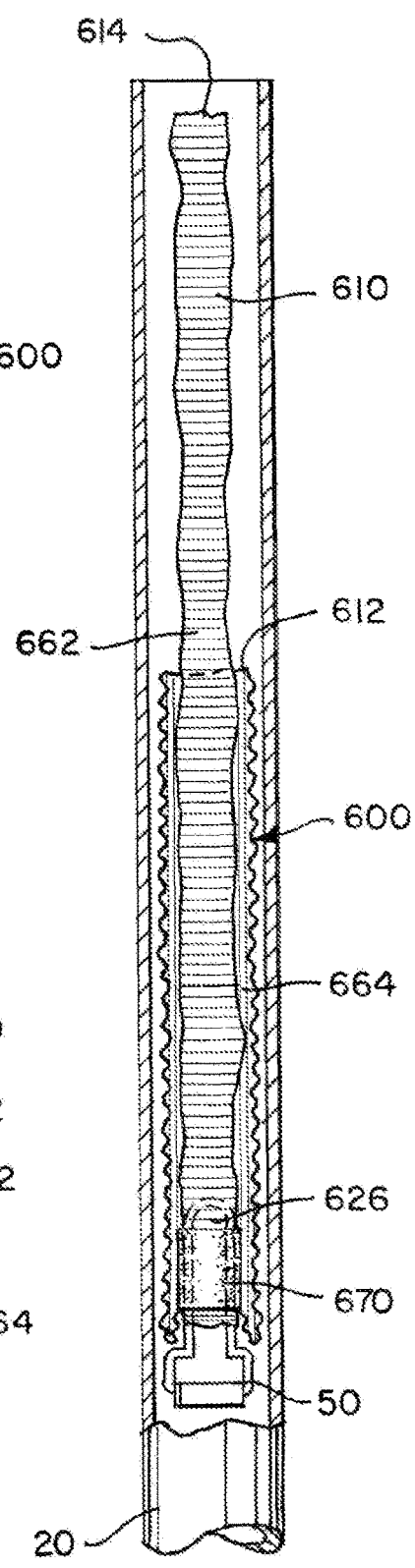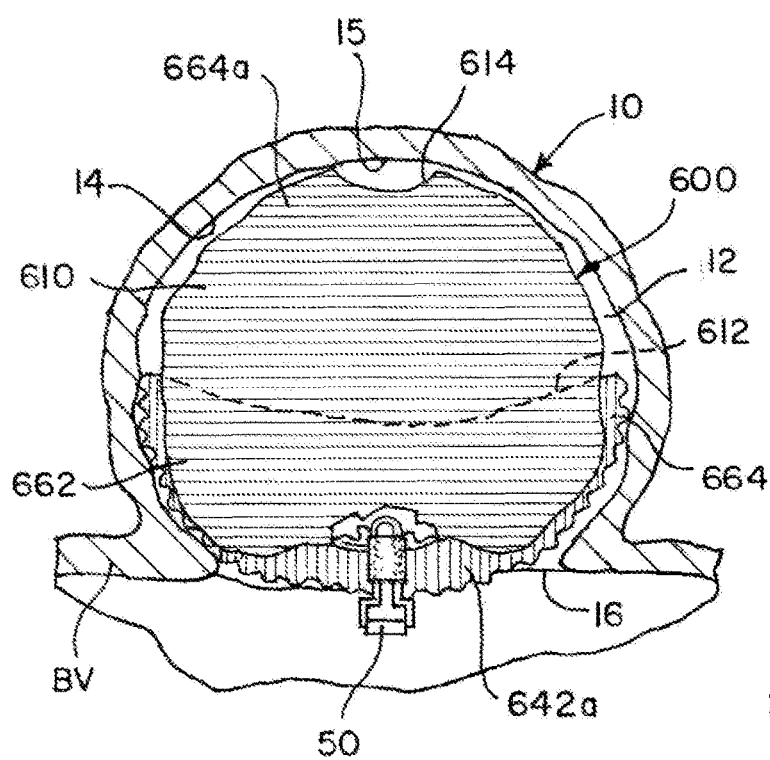

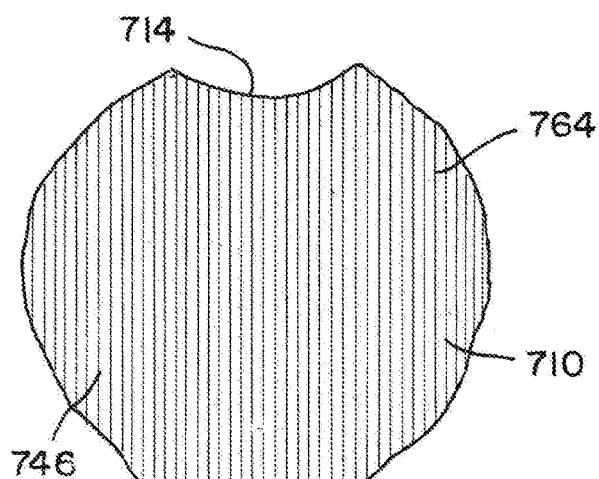
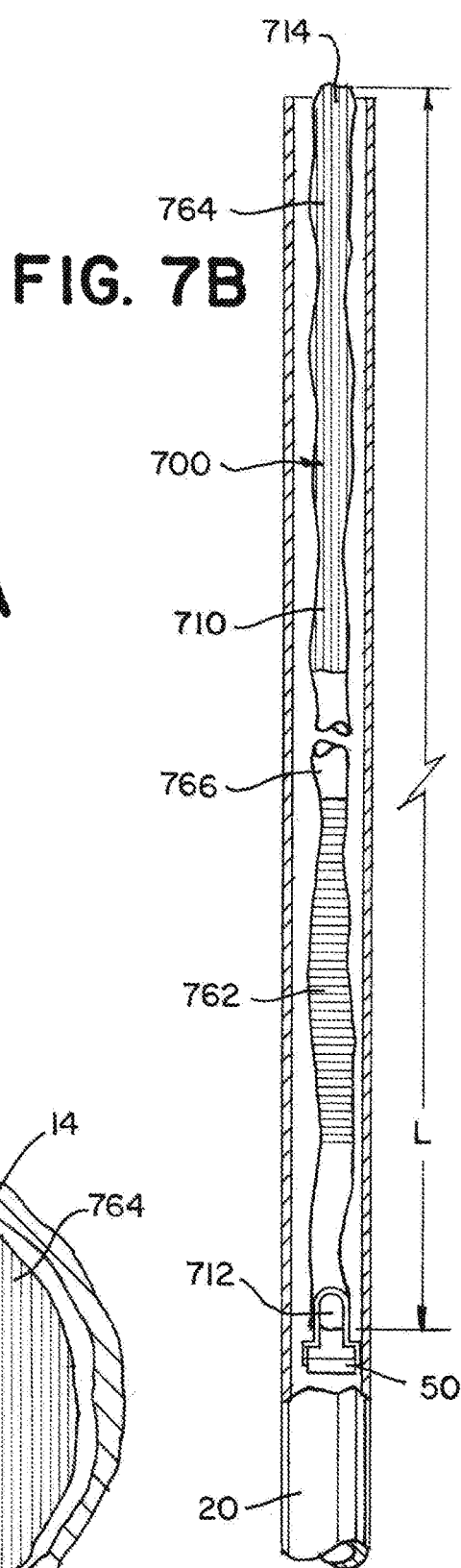
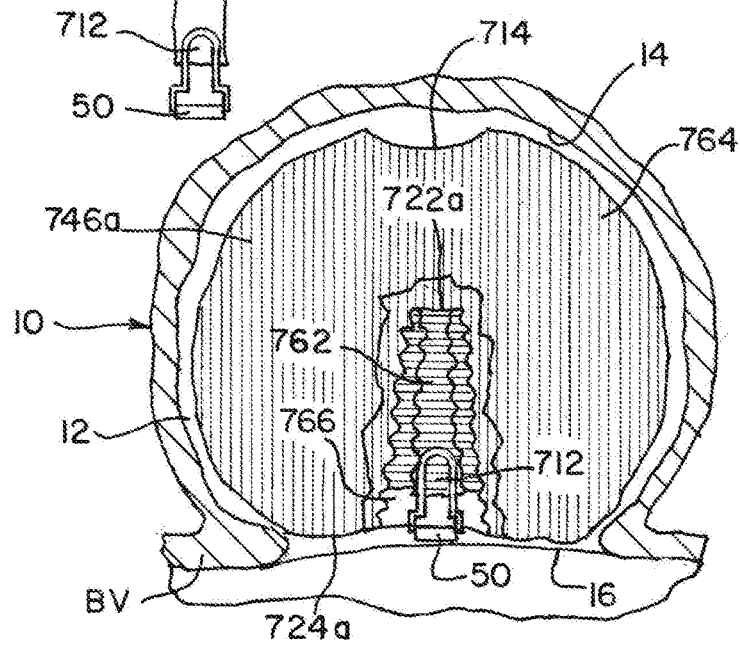
FIG. 7A
FIG. 7B
FIG. 7C

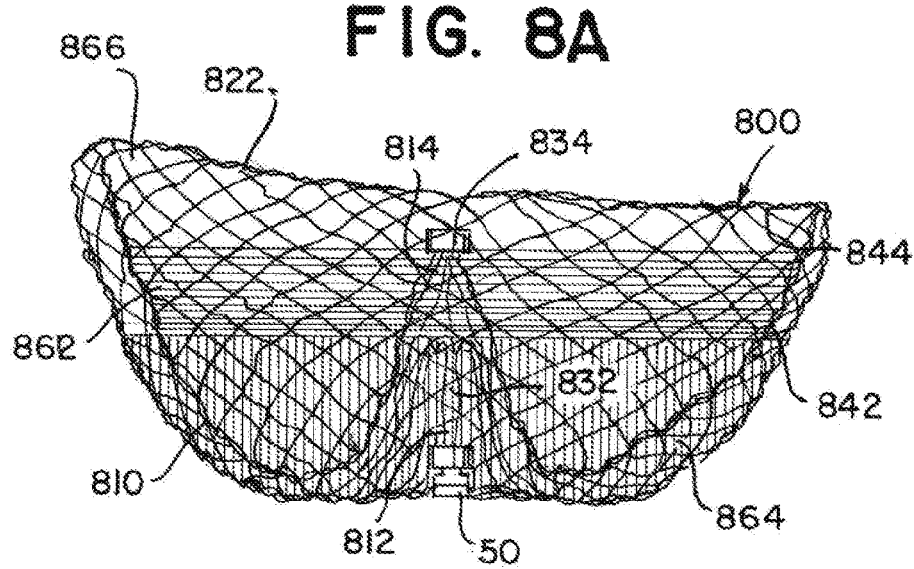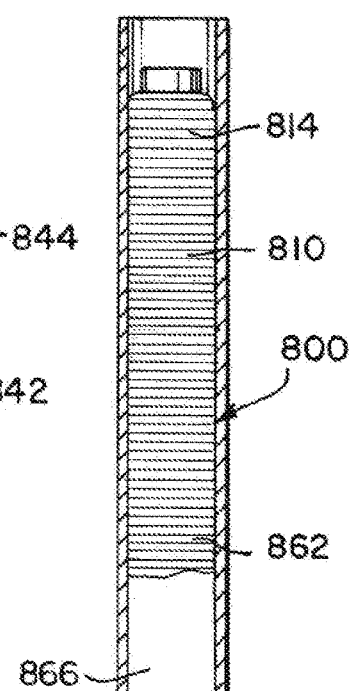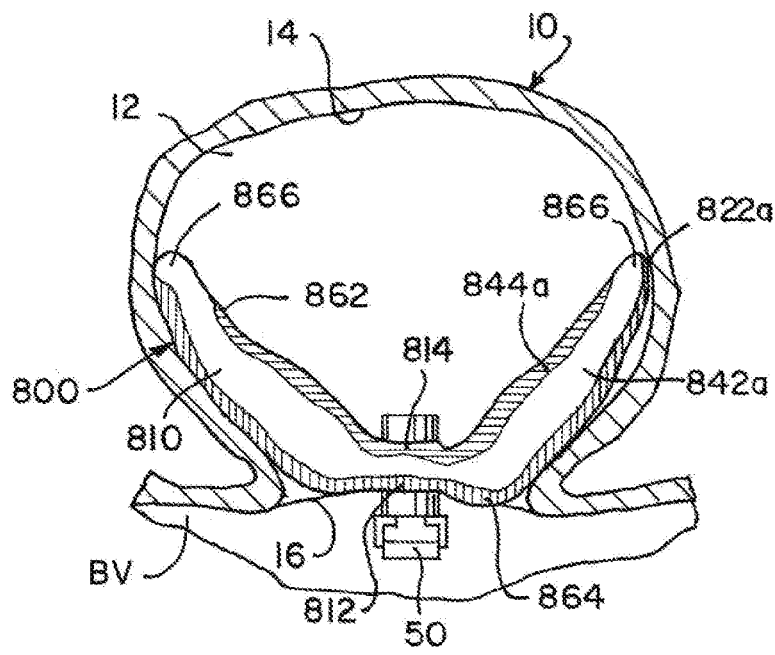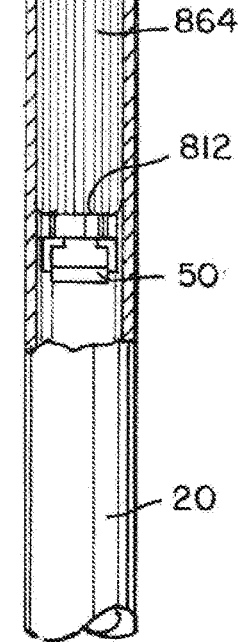

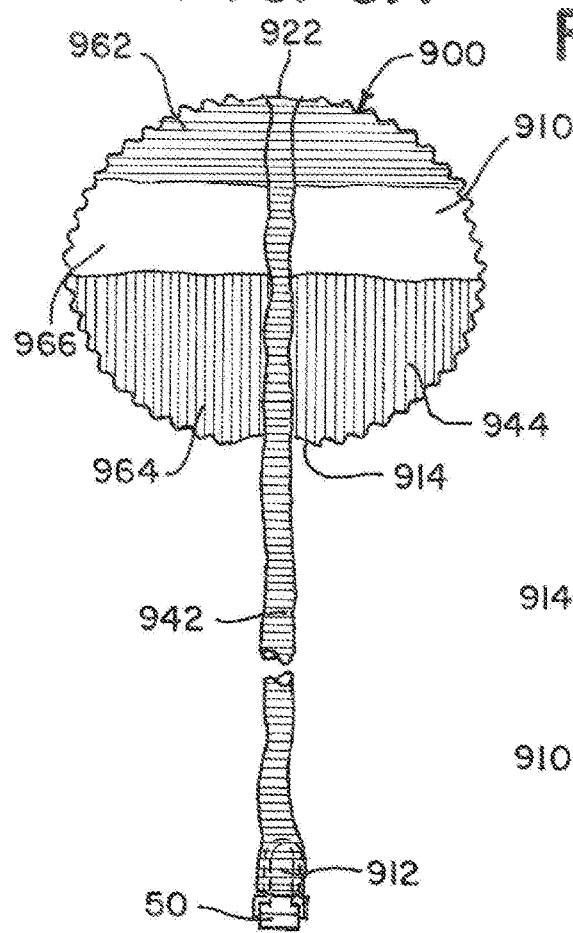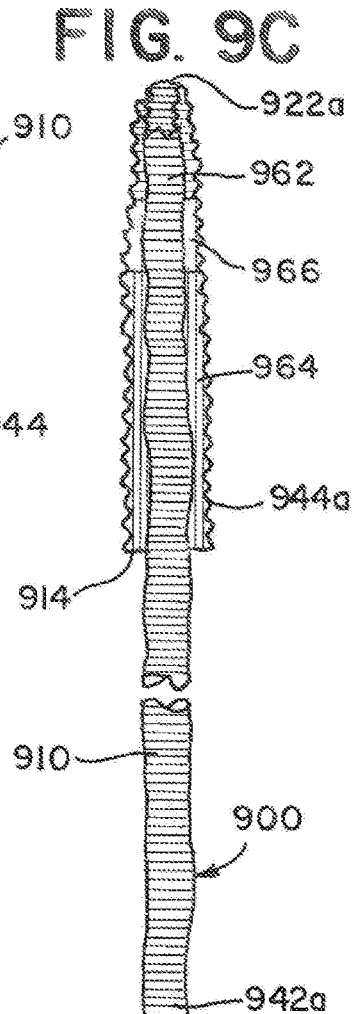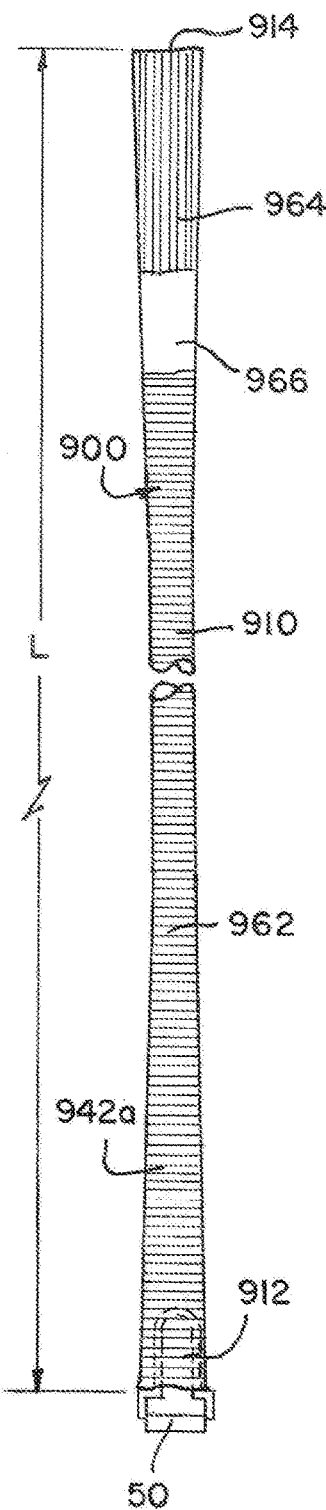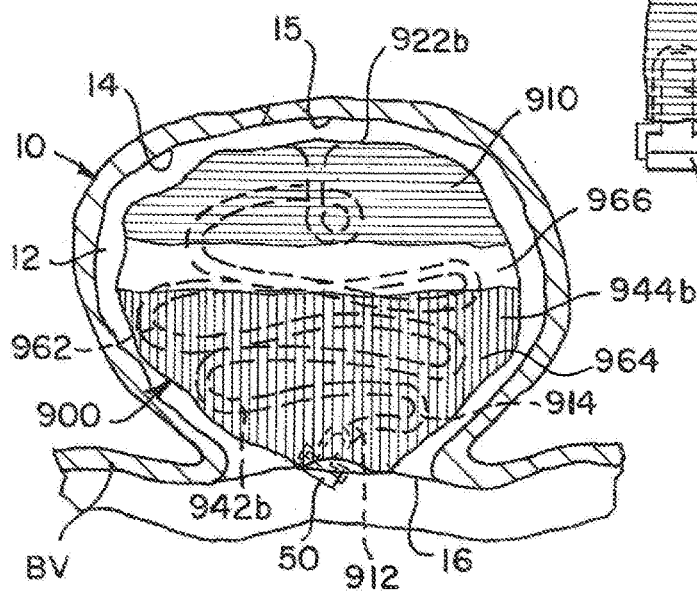

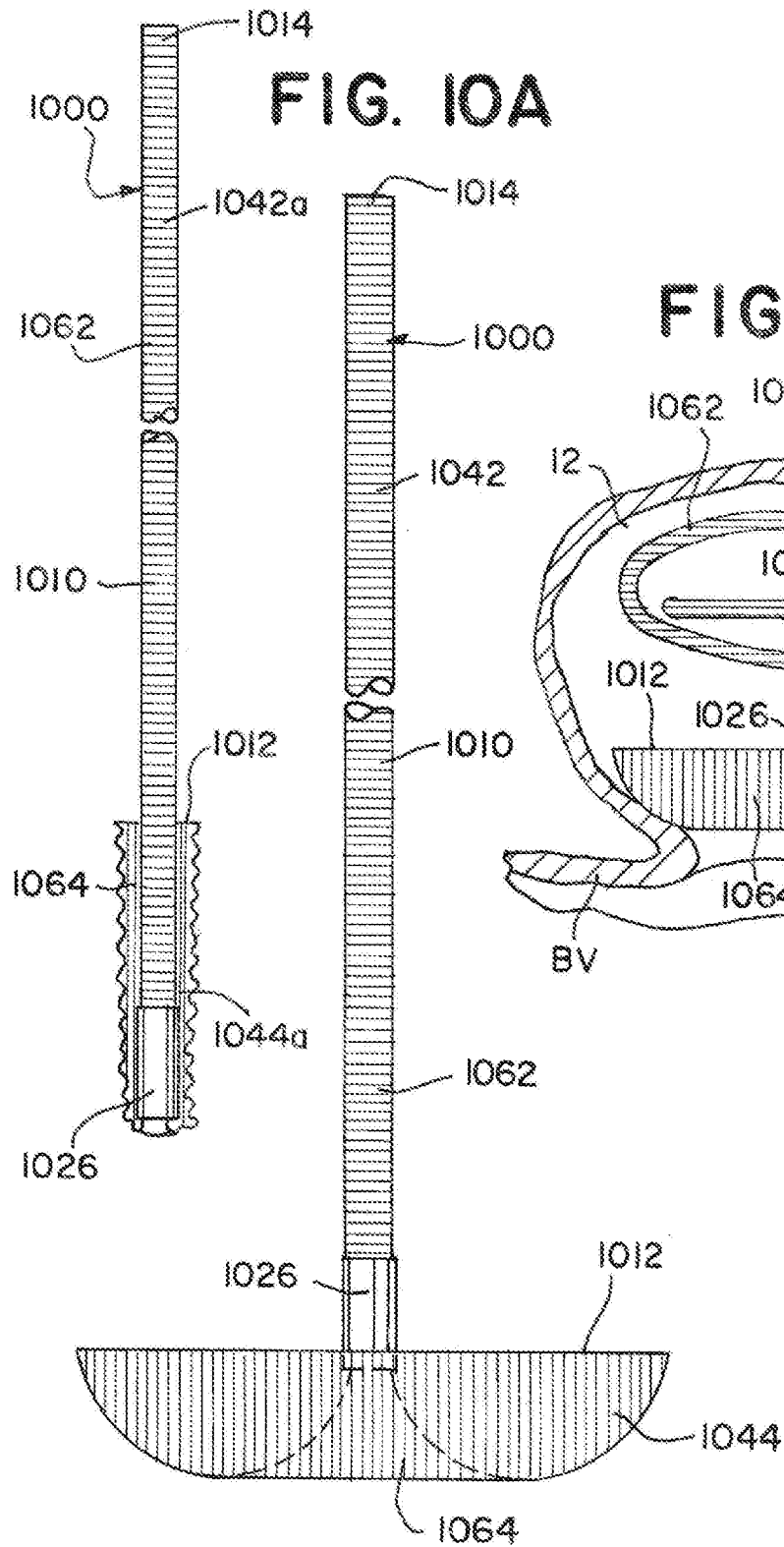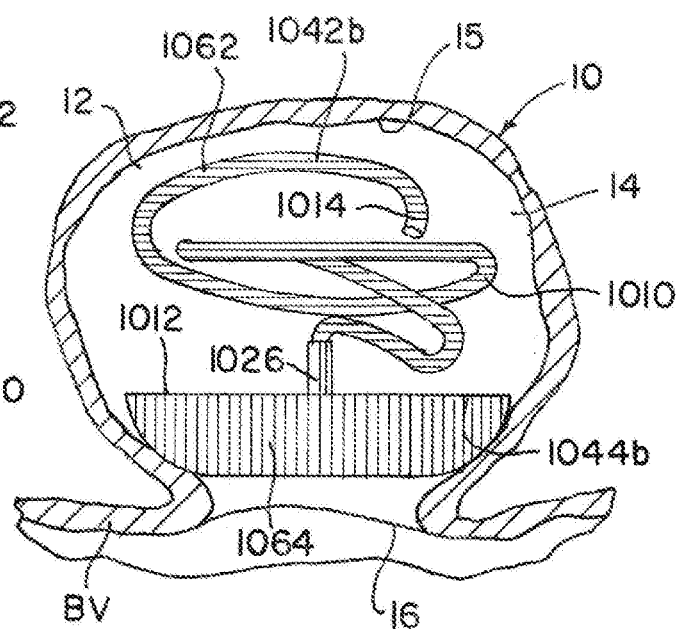

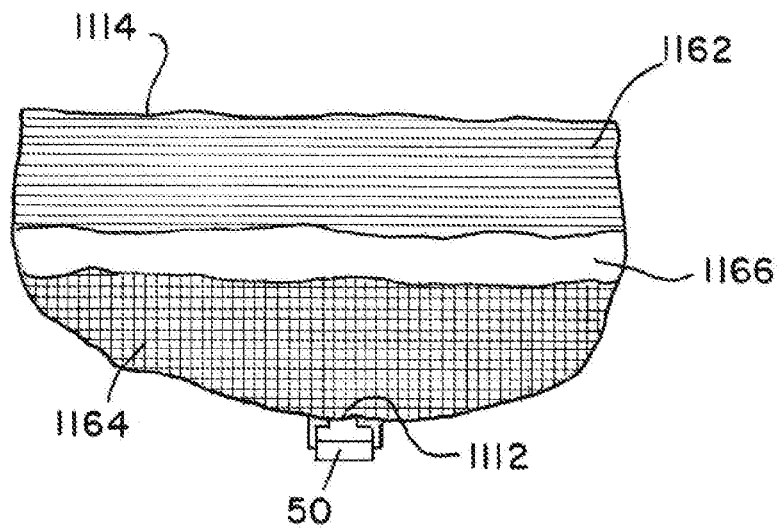
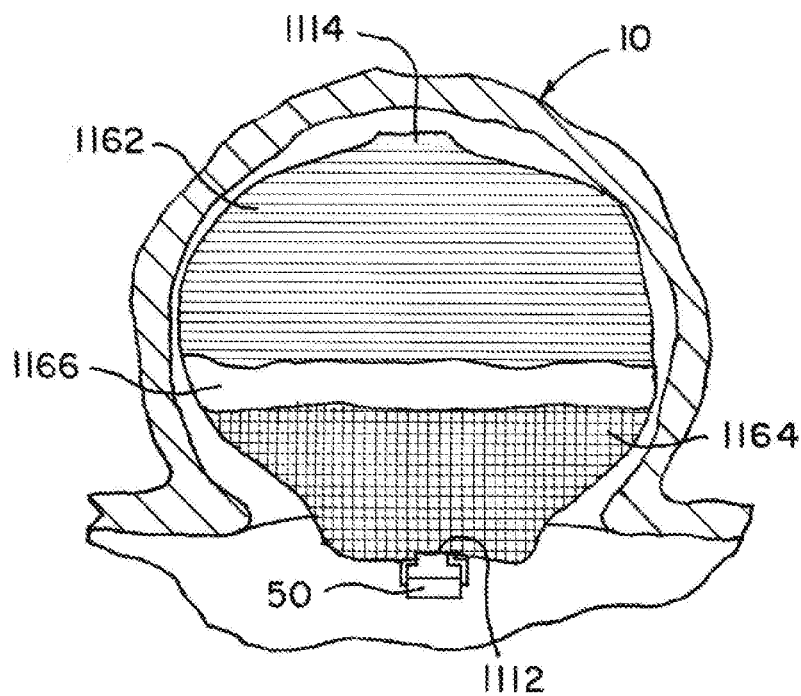
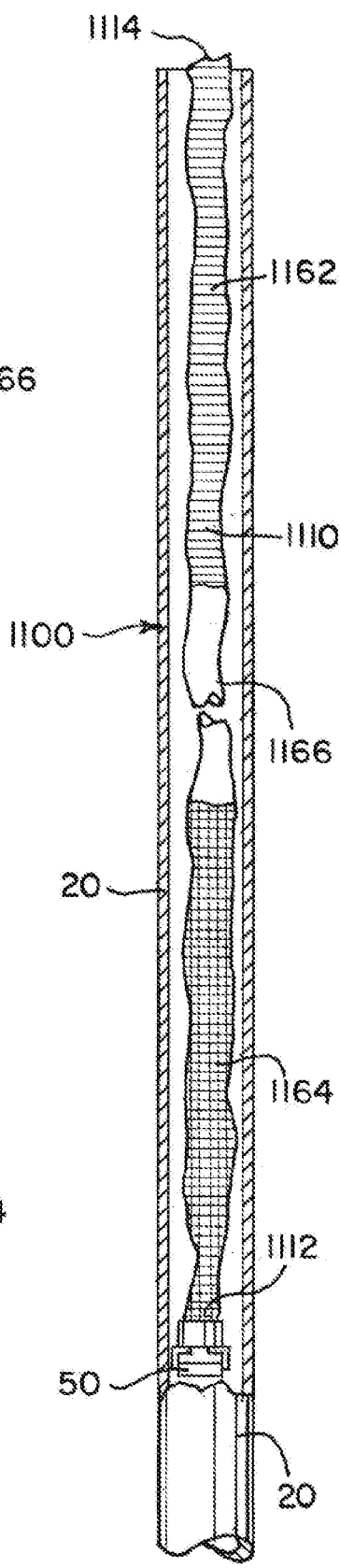

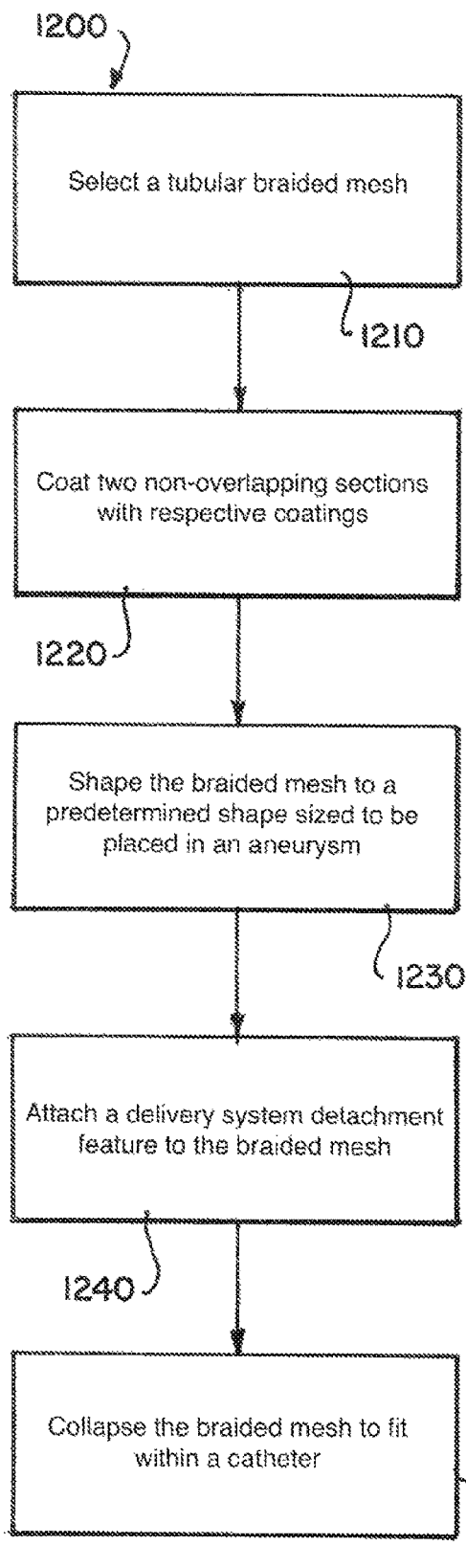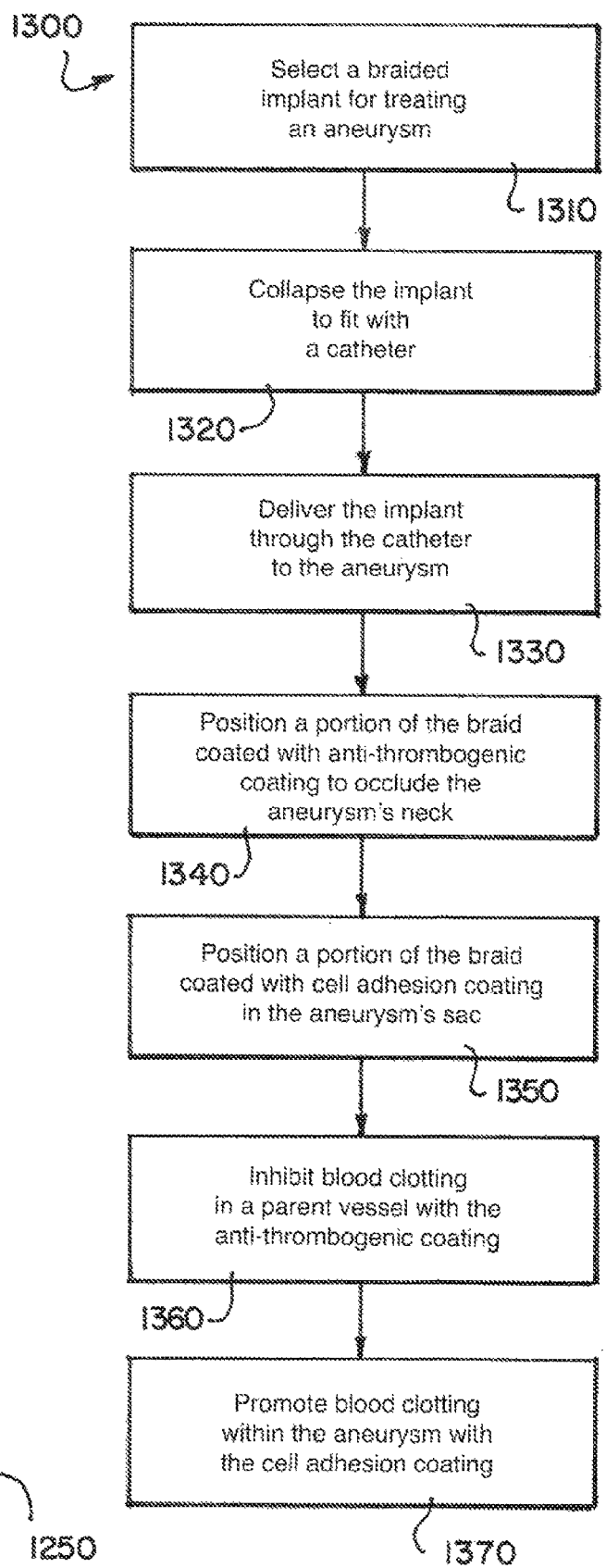

INTRASACCULAR ANEURYSM TREATMENT DEVICE WITH VARYING COATINGS

CROSS-REFERENCE TO RELATED APPLICATIONS

The present application is a continuation of, and claims priority under 35 U.S.C. § 120 to, U.S. patent application Ser. No. 16/595,050, filed Oct. 7, 2019, and is a continuation-in-part of, and claims priority under 35 U.S.C. § 120 to, U.S. patent application Ser. No. 16/997,543, filed on Aug. 19, 2020, which is a continuation of U.S. patent application Ser. No. 15/903,860, filed Feb. 23, 2018, which claims the benefit of U.S. Provisional Application No. 62/462,685, filed Feb. 23, 2017. The entire contents of these applications are fully incorporated herein by reference.

FIELD OF INVENTION

The present invention generally relates to medical instruments, and more particularly, to embolic implants for aneurysm therapy.

BACKGROUND

Cranial aneurysms can be complicated and difficult to treat due to their proximity to critical brain tissues. Prior solutions have included endovascular treatment whereby an internal volume of the aneurysm sac is removed or excluded from arterial blood pressure and flow. Current alternatives to endovascular or other surgical approaches can include intravascularly delivered treatment devices that fill the sac of the aneurysm with embolic material and/or block the entrance or neck of the aneurysm. Such approaches attempt to prevent blood flow into the aneurysm and promote formation of a thrombotic mass within the aneurysm.

Intravascularly delivered aneurysm treatment devices can typically be anchored in place within the aneurysm sac, within the blood vessel, or both. Intrasaccular aneurysm treatment devices, such as embolic coils, are anchored in place primarily within the aneurysm sac. Alternatives to embolic coils are being explored, for example a tubular braided implant is disclosed in US Patent Publication Number 2018/0242979, incorporated herein by reference.

Intrasaccular aneurysm treatment devices can typically include embolic material to promote formation of thrombotic mass within the aneurysm. Care must be taken when placing the intrasaccular devices so that embolic material and/or a clot formed thereon does not impede the flow of blood in the adjoining parent blood vessel, which can occur if the entrance to the aneurysm is overpacked. Conversely, if the entrance and/or sac is insufficiently packed, blood flow can persist into the aneurysm. Certain aneurysm morphology (e.g. wide neck, bifurcation, etc.) can be particularly challenging to treat, and current treatments of such morphology commonly rely on ancillary devices such a stents or flow diverters positioned within the adjoining blood vessel to cover the aneurysm entrance, protecting the adjoining blood vessel from becoming obstructed and retaining the intrasaccular device within the aneurysm. Placement of ancillary devices can be non-ideal as it can generally increase treatment time and complexity of the treatment procedure compared to treatments that can be performed without ancillary devices.

There is therefore a need for improved methods, implants, and systems for aneurysm treatment.

SUMMARY

It is an object of the present invention to provide systems, implants, and methods to meet the above-stated needs. Generally, it is an object of the present invention to provide an intrasaccular implant for treating an aneurysm having one or more coated regions, each coated region having a coating to either inhibit blood cell adhesion or promote blood cell adhesion. One or more regions of the implant that are designed to be implanted (and/or can potentially be implanted) in a position to contact blood from a parent blood vessel can be coated with a coating to inhibit blood cell adhesion to thereby reduce the likelihood that a thrombus can form on the implant that occludes the parent blood vessel. One or more regions of the implant that are designed to be contained within the aneurysm sac can be coated, abraded, or otherwise modified to promote blood cell adhesion to thereby promote thrombus formation within the aneurysm sac to reduce the likelihood of blood flow persisting into the aneurysm. The coatings can be applied linearly on separate lengths of a tubular braided implant. Coatings that are applied linearly on separate lengths of the tubular braid can be easier to apply compared to coatings that are applied opposite each other on an interior surface of the tubular braid and an outer surface of the tubular braid.

An example implant can include a braided mesh and two separate coatings. The braided mesh can be movable from a delivery configuration sized to traverse a catheter to an implanted configuration sized to be implanted in an aneurysm sac. The coatings can be disposed on the braided mesh, each respectively defining a section of the braided mesh, such that a section defined by one coating is separate from the section defined by the other coating. When the braid is in the implanted configuration, one of the coated sections can be positioned to occlude some or all of the aneurysm neck, and the other of the coated sections can be positioned within the aneurysm sac. The coated section positioned to occlude the aneurysm neck can be coated with an anti-thrombogenic and/or hydrophilic coating. The coated section positioned within the aneurysm sac can be coated with a cell adhesion coating.

The braided mesh can have, be movable to, and/or be constructed from a tubular shape having a single layer. The coated sections can be disposed along separate lengths of the braided mesh when the mesh is in the single-layer tubular shape. The coated sections can be non-overlapping.

The implant can also have one or more uncoated sections. An uncoated section can be positioned between the two coated sections.

When the braided mesh is in the implanted configuration, the coated section positioned to occlude the aneurysm neck can be positioned to form a barrier between the other coated section and a parent blood vessel.

When the braided mesh is in the implanted configuration, the coated section positioned for placement in the aneurysm sac can be shaped to form a sack within the aneurysm sac.

When the braided mesh is in the implanted configuration, the coated section positioned to occlude the aneurysm neck can also be positioned to contact the wall of the aneurysm, and the other coated section can be positioned to press the aforementioned coated section against the aneurysm wall.

An example method for designing, constructing, and/or configuring an implant for aneurysm treatment can include one or more of the following steps presented in no particular order, and the method can include additional steps not included here. A braided mesh can be selected. The selected braided mesh can be shaped as a tube. Two non-overlapping sections of the braided mesh can be respectively coated. When the braided mesh is shaped as a tube, the two coated sections can define two, separate, non-overlapping lengths along the axis of the tube. One of the sections can be coated with an anti-thrombogenic coating and the other section can be coated with a cell adhesion coating. The braided mesh can be shaped into a predetermined shape sized to be placed within an aneurysm sac. When in the predetermined shape, one of the sections can be shaped to extend across an aneurysm neck, contact an aneurysm wall, and at least partially surround the other section. The braided mesh can be collapsed to a delivery configuration sized to traverse a catheter positioned within vasculature.

An example method for treating an aneurysm can include one or more of the following steps presented in no particular order, and the method can include additional steps not included here. An implant having a braided mesh can be selected such that one portion of the braided mesh has an anti-thrombogenic coating and another portion has a cell adhesion coating. The braided mesh can be collapsed to a delivery configuration sized to traverse a catheter to the aneurysm. The braided mesh can be positioned within the catheter such that the anti-thrombogenic coated portion is positioned distally in relation to the blood cell adhesion coated portion. Alternatively, the braided mesh can be positioned within the catheter such that the anti-thrombogenic coated portion is positioned proximally in relation to the blood cell adhesion coated portion. In addition to either delivery configuration, or as an alternative delivery configuration, the braided mesh can be positioned within the catheter such that the anti-thrombogenic coated portion at least partially surrounds the cell adhesion coated portion.

The portion of the braided mesh with the anti-thrombogenic coating can be positioned to occlude the aneurysm's neck. The portion of the braided mesh with the cell adhesion coating can be placed within the aneurysm's sac. The portion of the braided mesh with the anti-thrombogenic coating can be positioned to obstruct communication between a parent blood vessel of the aneurysm and the blood cell adhesion coating. The portion of the braided mesh coated with the anti-thrombogenic coating can be positioned to extend beyond a plane defined by the aneurysm's neck. The portion of the braided mesh having the blood cell adhesion coating can form a sack within the aneurysm sac. Additionally, or alternatively, the braided mesh having the blood cell adhesion coating can loop within the aneurysm sac.

The portion of the braided mesh coated with the anti-thrombogenic coating can be positioned to contact the aneurysm's wall. The portion of the braided mesh coated with the cell adhesion coating can be positioned to press the first portion of the braided mesh to the aneurysm's wall.

Blood clotting within the parent blood vessel near the aneurysm's neck can be inhibited by the portion of the braided mesh coated with the anti-thrombogenic coating. Thrombosis can be induced within the aneurysm's sac with the portion of the braided mesh coated with the cell adhesion coating.

Blood flow through a rupture in the aneurysm's wall can be inhibited by the implant.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIGS. 1A through 1D are illustrations of a first implant having a coated braid in a predetermined shape, a delivery shape, and two implanted shapes respectively according to aspects of the present invention;

FIGS. 2A through 2C are illustrations of a second implant having a coated braid in a predetermined shape, a delivery shape, and an implanted shape respectively according to aspects of the present invention;

FIGS. 3A through 3C are illustrations of a third implant having a coated braid in a predetermined shape, a delivery shape, and an implanted shape respectively according to aspects of the present invention;

FIGS. 4A through 4C are illustrations of a fourth implant having a coated braid in a predetermined shape, a delivery shape, and an implanted shape respectively according to aspects of the present invention;

FIGS. 5A through 5C are illustrations of a fifth implant having a coated braid in a predetermined shape, a delivery shape, and an implanted shape respectively according to aspects of the present invention;

FIGS. 6A through 6C are illustrations of a sixth implant having a coated braid in a predetermined shape, a delivery shape, and an implanted shape respectively according to aspects of the present invention;

FIGS. 7A through 7C are illustrations of a seventh implant having a coated braid in a predetermined shape, a delivery shape, and an implanted shape respectively according to aspects of the present invention;

FIGS. 8A through 8C are illustrations of an eighth implant having a coated braid in a predetermined shape, a delivery shape, and an implanted shape respectively according to aspects of the present invention;

FIGS. 9A through 9D are illustrations of a ninth implant having a coated braid in a predetermined shape, two delivery shapes, and an implanted shape respectively according to aspects of the present invention;

FIGS. 10A through 10C are illustrations of a tenth implant having a coated braid in a predetermined shape, a delivery shape, and an implanted shape respectively according to aspects of the present invention;

FIGS. 11A through 11C are illustrations of an eleventh implant having a coated braid in a predetermined shape, a delivery shape, and an implanted shape respectively according to aspects of the present invention;

FIG. 12 is an illustration of a flow diagram illustrating method steps for designing, constructing, and/or configuring an implant according to aspects of the present invention; and FIG. 13 is an illustration of a flow diagram illustrating method steps for treating an aneurysm according to aspects of the present invention.

DETAILED DESCRIPTION

In known treatments of wide neck aneurysms, the aneurysm is typically treated by placing embolic coils within the aneurysm sac and placing a stent within the parent blood vessel across the aneurysm neck. The stent is necessary in many cases to inhibit the embolic coils from entering the parent blood vessel. If embolic coils enter the parent blood vessel, the coils can obstruct the vessel and/or clots can form on the coils within the blood vessel and create an obstruction in the parent blood vessel. Braided aneurysm intrasaccular implants can be used to treat wide neck aneurysms without requiring a stent to secure the braided implant at the aneurysm neck. In some treatments, to provide a secure seal to block blood flow into the aneurysm neck, it can be desirable to position a portion of the braided intrasaccular implant to partially protrude into the parent blood vessel. However, for braid material having cell adhesion properties, clots can potentially form on the protruded portion within the parent vessel and obstruct the parent blood vessel. Braided aneurysm intrasaccular implants, in some cases, rely on less embolic mass within the aneurysm sac compared to embolic coils, and in those cases, blood stasis may not occur as quickly within the aneurysm sac compared to a treatment wherein the aneurysm sac is densely packed with embolic coils.

Aspects of the present invention are directed to address the above challenges. In examples presented herein, a braided aneurysm implant can be coated with an anti-thrombogenic coating (such as a hydrophilic coating), a cell adhesion coating, or both. The braid of the implant can be formed from a generally tubular, single layer, linear weave. When used herein, the terms "tubular" and "tube" are to be construed broadly and are not limited to a structure that is a right cylinder or strictly circumferential in cross-section or of a uniform cross-section throughout its length. For example, the tubular structure or system is generally illustrated as a substantially right cylindrical structure. However, the tubular system may have a tapered or curved outer surface without departing from the scope of the present invention.

Each coating can be disposed on a linear section of the braid. The braid can have a predetermined shape that is shaped to treat a predetermined range of aneurysm sizes, a delivery shape sized to traverse a lumen of a catheter to an aneurysm, and an implanted shape that is based on the predetermined shape and the shape of the sac and neck of the aneurysm.

When in the implanted shape, a portion of the braid can occlude the neck of the aneurysm, and this portion can be coated with the anti-thrombogenic coating. Implanted this way, if the braid protrudes into the parent vessel, the anti-thrombogenic coating can be effective to prevent thrombus from forming on the protruding braid portion and thereby preventing occlusion of the parent blood vessel by such a thrombus formation. Additionally, or alternatively, a portion of the braid contained within the aneurysm sac can be coated with a cell adhesion coating. The cell adhesion coating can be effective to promote thrombus formation within the aneurysm sac. In some treatments, a portion of the braid having cell adhesion coating thereon can be placed across a rupture in the aneurysm's wall, and the cell adhesion coated braid portion can be effective to inhibit and ultimately eliminate blood flow out of the sac through the rupture.

Turning to the figures, FIGS. 1A through 11C are illustrations of ten implants 100, 200, 300, 400, 500, 600, 700, 800, 900, 1000, 1100 each having a braided mesh 110, 210, 310, 410, 510, 610, 710, 810, 910, 1010, 1110 having two coated sections—one section with an anti-thrombogenic coating 164, 264, 364, 464, 564, 664, 764, 864, 964, 1064, 1164 and another section with a cell adhesion coating 162, 262, 362, 462, 562, 662, 762, 862, 962, 1062, 1162. Each braided mesh can be formed of a material that is embolic, promoting cell adhesion. For instance, braided mesh can include strands of nitinol, platinum, drawn filed tubing (DFT), and/or other braided materials as would be appreciated and understood by a person of ordinary skill in the art. The section 162, 262, 362, 462, 562, 662, 762, 862, 962, 1062, 1162 of each braided mesh can be modified to have enhanced cell adhesion properties compared to the material of the braided mesh. For instance, the section can be coated with cell adhesion coating and/or can be abraded or otherwise shaped to have a rough surface to promote cell adhesion. For instance, the braid can be coated with polyglycolic acid (PGA), poly(lactic-co-glycolic acid) (PLGA), and/or other such coating as would be appreciated and understood by a person of ordinary skill in the art. A hydrophyilic hydrogel expandable upon contact with blood can be used as a cell adhesion coating. The section 164, 264, 364, 464, 564, 664, 764, 864, 964, 1064, 1164 of each braided mesh can have enhanced inhibited cell adhesion properties compared to the material of the braided mesh. For instance, the section can be coated with anti-thrombogenic coating such as Heparin, Phosphorylcholine, a hydrophilic coating, or other such coating as would be appreciated and understood by a person of ordinary skill in the art.

Coatings can be applied by dipping, spraying, or other means as would be appreciated and understood by a person of ordinary skill in the art. Abrading can be applied in place of, or in addition to a cell adhesion coating in sections 162, 262, 362, 462, 562, 662, 762, 862, 962, 1062, 1162 with enhanced cell adhesion properties. For ease of discussion, sections with enhanced cell adhesion properties are described herein as "coated", however, it is to be understood that abrading or otherwise enhancing the cell adhesion properties can be used in addition to, or in place of coating.

A coating (or other surface enhancement) can be applied to only one side of the braid (e.g. either within the lumen of a tubular braid or on the outer surface of the tubular braid), or a coating can be applied to both sides of the braid. In some examples, one coating can be applied to one side of the braid and a second coating can be applied to the other side of the braid. In some examples, two coatings can be applied to the same side of the braid. In some examples, one coating can be applied to both sides of the braid and a second coating can be applied to only one side of the braid. In some examples, two coatings can each be applied to both sides of the braid.

Examples presented herein primarily illustrate two coated regions, however, the braid can be coated or abraded, or otherwise enhanced in multiple lengths according to aspects of the present disclosure.

In the examples illustrated, each braided mesh 110, 210, 310, 410, 510, 610, 710, 810, 910, 1010, 1110 can have a delivery shape that is sized to traverse a lumen of a catheter 20 to an aneurysm 10, 10a, 10b and an implanted shape that is sized to be implanted in the aneurysm sac 12, 12a, 12b. Each braided mesh 110, 210, 310, 410, 510, 610, 710, 810, 910, 1010, 1110 can also have a predetermined shape that is shaped to treat a predetermined range of aneurysm sizes. When the implant 100, 200, 300, 400, 500, 600, 700, 800, 900, 1000, 1100 exits the catheter 20 and enters the aneurysm 10, 10a, 10b, the braid 110, 210, 310, 410, 510, 610, 710, 810, 910, 1010, 1110 can move toward the predetermined shape and be confined by the shape of the aneurysm walls 14, 14a, 14b and aneurysm neck 16, 16a, 16b such that the resulting implanted shape of the braid is based on the predetermined shape and the anatomy of the aneurysm.

In the examples illustrated, coatings can be positioned on the braided mesh 110, 210, 310, 410, 510, 610, 710, 810, 910, 1010, 1110 such that when implanted, the section 164, 264, 364, 464, 564, 664, 764, 864, 964, 1064, 1164 coated with anti-thrombogenic coating is placed at the aneurysm neck 16, 16a, 16b and/or the section 162, 262, 362, 462, 562, 662, 762, 862, 962, 1062, 1162 coated with cell adhesion coating is confined within the aneurysm sac 12, 12a, 12b. The position of the coated section(s) when implanted can be predetermined to a large extent by virtue of the predetermined shape and the anatomy of the aneurysm 10, 10a, 10b being known. In other words, the coated section(s) 162, 262, 362, 462, 562, 662, 762, 862, 962, 1062, 164, 264, 364, 464, 564, 664, 764, 864, 964, 1064, 1164 can be positioned in relation to the predetermined shape of the braid 110, 210, 310, 410, 510, 610, 710, 810, 910, 1010, 1110 such that when the braid is implanted, each coated section can be predictably placed either to occlude the aneurysm neck 16, 16a, 16b or to be contained within the aneurysm sac 12, 12a, 12b.

In the examples illustrated, each implant 100, 200, 300, 400, 500, 600, 700, 800, 900, 1000, 1100 can be formed from a generally tubular, single-layer braided mesh 110, 210, 310, 410, 510, 610, 710, 810, 910, 1010, 1110. Each tubular braid 110, 210, 310, 410, 510, 610, 710, 810, 910, 1010, 1110 can respectively have a first end 112, 212, 312, 412, 512, 612, 712, 812, 912, 1012, 1112 and a second end 114, 214, 314, 414, 514, 614, 714, 814, 914, 1014, 1114. The coatings can be applied in two separate linear sections 162, 262, 362, 462, 562, 662, 762, 862, 962, 1062, 164, 264, 364, 464, 564, 664, 764, 864, 964, 1064, 1164 of the braided mesh between the two ends of the braided mesh.

In some of the illustrated examples, some implants 100, 200, 400, 500, 700, 800, 900, 1100 can include an uncoated section 166, 266, 466, 566, 766, 866, 966, 1166 between the two coated sections 162, 262, 462, 562, 762, 862, 962, 164, 264, 464, 564, 764, 864, 964, 1164. The section 162, 262, 462, 562, 662, 762, 862, 962, 1162 of each braided mesh 110, 210, 410, 510, 610, 710, 810, 910, 1110 coated with cell adhesion coating can have enhanced cell adhesion properties compared to the uncoated section 166, 266, 466, 566, 766, 866, 966, 1166 of that braided mesh. The section 164, 264, 464, 564, 664, 764, 864, 964, 1164 of each braided mesh coated with anti-thrombogenic coating can have inhibited cell adhesion properties compared to the uncoated section 166, 266, 466, 566, 766, 866, 966, 1166 of that braided mesh. In some applications it can be advantageous to position an uncoated section on a portion of the braid that can be positioned to be in communication with the parent blood vessel or positioned within the aneurysm sac depending on the aneurysm morphology and the positioning of the braid within the aneurysm. In some applications it can be advantageous to include an uncoated section to define a boundary between two coated sections so that the two coated sections are non-overlapping.

In some applications, a portion of the section 164, 264, 364, 464, 564, 646, 764, 864, 964, 1064, 1164 coated with anti-thrombogenic coating be purposefully or unintentionally positioned to extend to a proximal side of a plane 18 defining a boundary between an aneurysm 10, 10a, 10b and a parent blood vessel BV as illustrated in FIG. 1C. In such applications, the anti-thrombogenic coating can be effective to inhibit formation of thrombosis within the parent blood vessel BV on the portion extending beyond the plane 18.

Implants 100, 200, 300, 400, 500, 600, 700, 800, 900, 1000, 1100 presented herein, in some applications, can be effective to inhibit blood flow circulation in the aneurysm. By inhibiting blood flow circulation, the implant can be effective to inhibit blood flow through a rupture in the aneurysm, particularly for ruptures near the distal portion 15, 15a, 15b, thereby promoting healing of the rupture and inhibiting blood flow through the rupture.

In the examples illustrated, each implant 100, 200, 300, 400, 500, 600, 700, 800, 900, 1000, 1100 can include a locking portion/detachment feature 50 that can be engaged to a delivery system (not illustrated) to facilitate delivery of the implant through the catheter 20 to the aneurysm 10, 10a, 10b. The locking portion/detachment feature 50 can be disengaged from the delivery system when the implant is positioned within the aneurysm 10, 10a, 10b to allow the delivery system to be extracted. A delivery system suitable for delivering the example implants illustrated herein is disclosed in U.S. patent application Ser. No. 15/964,857 incorporated herein by reference. As would be appreciated and understood by a person of ordinary skill in the art, many other alternative delivery systems can be suitable for delivering example implants disclosed herein.

In the examples illustrated, each shape illustrated can be substantially radially symmetrical. Shapes are illustrated in profile unless otherwise stated. Some shapes are illustrated in cross-section. Examples are illustrated with portions of and aneurysm 10, 10a, 10b or a catheter 20 cut away or in cross-section.

FIGS. 1A through 4C are illustrations of implants 100, 200, 300, 400 each having a braid 110, 210, 310, 410 having a predetermined shape, a delivery shape, and one or more implanted shapes similar to corresponding shapes disclosed in U.S. patent application Ser. No. 16/418,199 incorporated herein by reference.

FIGS. 1A through 1D are illustrations of an implant 100 that can have braid 110 having a predetermined shape as illustrated in FIG. 1A, a delivery shape as illustrated in FIG. 1B and two distinct implanted shapes as illustrated in FIG. 1C and FIG. 1D. FIGS. 1A, 1C, and 1D illustrate the implant 100 in cross-section. The implant 100 can treat a range of aneurysm sizes including a larger aneurysm 10a as illustrated in FIG. 1C and a smaller aneurysm 10b as illustrated in FIG. 1D. The braid can have one or more coated sections 162, 164. The braid 110 can have a section 164 having an anti-thrombogenic coating and/or a section 162 having a cell adhesion coating. Two coated sections 162, 164 can be separated by an uncoated section 166.

As illustrated in FIG. 1A, the braid 110 can have two inversions 122, 124 and three segments 142, 144, 146. An outer segment 142 can extend between an open end 114 of the braid 110 and a proximal inversion 122. A middle segment 144 can extend between the proximal inversion 122 and a distal inversion 124. An inner segment 146 can extend between the distal inversion 124 and a pinched end 112 of the braid 110. The middle segment 144 can have a constriction 126 and one or more bends 132, 134.

In the predetermined shape, the section 164 coated with anti-thrombogenic coating can extend across the proximal inversion 122 and include some or all of the outer segment 142 and a first portion of the middle segment 144. The uncoated section 166 can extend across the constriction 126 and include a second portion of the middle segment 144. The section 162 coated with cell adhesion coating can extend across the distal inversion 124 and can include a third portion of the middle segment 144 and some or all of the inner segment 146.

As illustrated in FIG. 1B, the braid 110 can be extended to a single-layer tubular shape during delivery. In the delivery shape, the coated sections 162, 164 can each respectively occupy separate, non-overlapping portions of the length L of the braid. The section 162 coated with cell adhesion coating can be positioned proximally in relation to the section 164 coated with anti-thrombogenic coating. Configured thusly, the section 164 coated with anti-thrombogenic coating can exit the catheter 20 into an aneurysm 10a, 10b (see FIGS. 1C and 1D) prior to the section 162 coated with cell adhesion coating. Each respective coating can be disposed on the outer surface of the braid 110 when the braid is in the single-layer tubular shape. Additionally, cell adhesion coating can be applied in the respective section 162 on the inner surface of the braid 110 when the braid is in the single-layer tubular shape.

As illustrated in FIGS. 1C and 1D, the braid 110 can shape into two distinct implanted shapes. Each implanted shape can be based on the predetermined shape illustrated in FIG. 1A and the anatomy of the respective aneurysm 10a, 10b illustrated in FIGS. 1C and 1D. In the implanted shape illustrated in FIG. 1C, the braid 110 can have a proximal inversion 122a and a distal inversion 124a corresponding to the proximal inversion 122 and the distal inversion 124 of the predetermined shape illustrated in FIG. 1A and three segments 142a, 144a, 146a corresponding to the three segments 142, 144, 146 illustrated in FIG. 1A. The middle segment 144a can form a sack within the aneurysm sac 12a as illustrated in FIG. 1C. In the implanted shape illustrated in FIG. 1D, the braid 110 can have a proximal inversion 122b corresponding to the proximal inversion 122 of the predetermined shape illustrated in FIG. 1A, a distal inversion 124b corresponding to the bend 134 of the predetermined shape, an outer segment 142b corresponding to the outer segment 142 of the predetermined shape, a middle segment 144b corresponding to a portion of the middle segment 144 of the predetermined shape, and an inner segment 146b corresponding to a portion of the middle segment 144 and the inner segment 146 of the predetermined shape.

In either implanted shape, the section 164 coated with anti-thrombogenic coating can be positioned to occlude some or all of the aneurysm neck 16a, 16b. The section 164 coated with anti-thrombogenic coating can form a barrier between the section 162 coated with cell adhesion coating and a parent blood vessel BV. The section 164 coated with anti-thrombogenic coating can extend to a proximal side of a plane 18 defining a boundary between the aneurysm 10a, 10b and the parent blood vessel BV. The section 164 coated with anti-thrombogenic coating can inhibit blood clotting within the parent blood vessel BV near the aneurysm neck 16a, 16b. A portion of the section 164 coated with anti-thrombogenic coating can be positioned to contact the aneurysm wall 14a, 14b. The anti-thrombogenic coating can be disposed on a side of the braid 110 that is in communication with the parent blood vessel BV and in contact with the aneurysm wall 14a, 14b.

In either implanted shape, the section 162 coated with cell adhesion coating can be contained within the aneurysm sac 12a, 12b. The section 162 coated with cell adhesion coating can press the section 164 coated with anti-thrombogenic coating to the aneurysm wall 14a, 14b. The section 162 coated with cell adhesion coating can induce thrombosis within the aneurysm sac 12a, 12b. The cell adhesion coating can be disposed on a side of the braid 110 that is interior to the sack formed by the middle segment 144a illustrated in FIG. 1C or between the middle 144b and inner 146b segments illustrated in FIG. 1D. Additionally, the cell adhesion coating can be disposed on a side of the braid 110 that is in contact with the aneurysm wall 14a as illustrated in FIG. 1C or on a side of the inner segment 146b that is facing inwardly into the aneurysm sac 12b as illustrated in FIG. 1D.

In treatments wherein the aneurysm 10a has a rupture near a distal portion 15a of the aneurysm wall 14a, a portion of the section 162 with cell adhesion coating that is positioned across and/or near the rupture can be effective to form a clot over the rupture and thereby inhibit blood flow through the rupture. In the implanted shape illustrated in FIG. 1C, the implant 100 can thereby be effective to inhibit blood flow through such a rupture.

In either implanted shape, the uncoated section 166 can be positioned near the center of the aneurysm neck 16a, 16b.

FIGS. 2A through 2C are illustrations of an implant 200 that can have braid 210 having a predetermined shape as illustrated in FIG. 2A, a delivery shape as illustrated in FIG. 2B, and an implanted shape as illustrated in FIG. 2C. FIGS. 2A and 2C illustrate the implant 200 in cross-section. The braid 210 can have a section 264 having an anti-thrombogenic coating and/or a section 262 having a cell adhesion coating. Two coated sections 262, 264 can be separated by an uncoated section 266.

As illustrated in FIG. 2A, the braid 210 can have two inversions 222, 224 and three segments 242, 244, 248. An outer segment 242 can extend between an open end 214 of the braid 210 and a proximal inversion 222. A middle segment 244 can extend between the proximal inversion 222 and a distal inversion 224. An inner segment 248 can extend between the distal inversion 224 and a pinched end 212 of the braid 210. The middle segment 244 can have a constriction 226.

In the predetermined shape, the section 264 coated with anti-thrombogenic coating can extend across the proximal inversion 222 and include some or all of the outer segment 242 and a first portion of the middle segment 244. The uncoated section 266 can extend across the constriction 226 and include a second portion of the middle segment 244. The section 262 coated with cell adhesion coating can extend across the distal inversion 224 and can include a third portion of the middle segment 244 and some or all of the inner segment 246.

As illustrated in FIG. 2B, the braid 210 can be extended to a single-layer tubular shape during delivery. In the delivery shape, the coated sections 262, 264 can each respectively occupy separate, non-overlapping portions of the length L of the braid. The section 262 coated with cell adhesion coating can be positioned proximally in relation to the section 264 coated with anti-thrombogenic coating. Configured thusly, the section 264 coated with anti-thrombogenic coating can exit the catheter 20 into an aneurysm 10 (see FIG. 2C) prior to the section 262 coated with cell adhesion coating. Each respective coating can be disposed on the outer surface of the braid 210 when the braid is in the single-layer tubular shape.

As illustrated in FIG. 2C, the braid 210 can shape into an implanted shape. The implanted shape can be based on the predetermined shape illustrated in FIG. 2A and the anatomy of the aneurysm 10 illustrated in FIG. 2C. In the implanted shape, the braid 210 can have a proximal inversion 222a and a distal inversion 224a corresponding to the proximal inversion 222 and the distal inversion 224 of the predetermined shape illustrated in FIG. 2A and three segments 242a, 244a, 248a corresponding to the three segments 242, 244, 248 illustrated in FIG. 2A. The middle segment 244a can form a sack within the aneurysm sac 12. The inner segment 248a can form a compaction resistant post within the aneurysm sac 12.

In the implanted shape, the section 264 coated with anti-thrombogenic coating can be positioned to occlude some or all of the aneurysm neck 16. The section 264 coated with anti-thrombogenic coating can form a barrier between the section 262 coated with cell adhesion coating and a parent blood vessel BV. The section 264 coated with anti-thrombogenic coating can inhibit blood clotting within the parent blood vessel BV near the aneurysm neck 16. A portion of the section 264 coated with anti-thrombogenic coating can be positioned to contact the aneurysm wall 14. The anti-thrombogenic coating can be disposed on a side of the braid 210 that is in communication with the parent blood vessel BV and in contact with the aneurysm wall 14.

In the implanted shape, the section 262 coated with cell adhesion coating can be contained within the aneurysm sac 12. The section 262 coated with cell adhesion coating can press the section 264 coated with anti-thrombogenic coating to the aneurysm wall 14. The section 262 coated with cell adhesion coating can induce thrombosis within the aneurysm sac 12. The cell adhesion coating can be disposed on a side of the braid 210 that is interior to the sack formed by the middle segment 244a and on an outer surface of the compaction resistant post 248a.

In treatments in which the aneurysm 10 has a rupture near a distal portion 15 of the aneurysm wall 14, a portion of the section 262 with cell adhesion coating that is positioned across and/or near the rupture can be effective to form a clot over the rupture and thereby inhibit blood flow through the rupture. The implant 200 can thereby be effective to inhibit blood flow through such a rupture.

In the implanted shape, the uncoated section 266 can be positioned near the center of the aneurysm neck 16.

FIGS. 3A through 3C are illustrations of an implant 300 that can have a braid 310 having a predetermined shape as illustrated in FIG. 3A, a delivery shape as illustrated in FIG. 3B and an implanted shape as illustrated in FIG. 3C. FIGS. 3A and 3C illustrate the implant 300 in cross-section. The braid 310 can have a section 364 having an anti-thrombogenic coating and/or a section 362 having a cell adhesion coating. Although not illustrated, the two coated sections 362, 364 can be separated by an uncoated section.

As illustrated in FIG. 3A, the braid 310 can have two inversions 322, 324 and three segments 342, 344, 346. An outer segment 342 can extend between an open end 314 of the braid 310 and a proximal inversion 322. A middle segment 344 can extend between the proximal inversion 322 and a distal inversion 324. An inner segment 346 can extend between the distal inversion 324 and a pinched end 312 of the braid 310. The middle segment 344 can have a constriction 326 and undulating pattern. The undulating pattern can be radially symmetrical to form a honeycomb shape.

In the predetermined shape, the section 364 coated with anti-thrombogenic coating can extend across the proximal inversion 322 and include some or all of the outer segment 342 and a first portion of the middle segment 344. The section 362 coated with cell adhesion coating can extend across the distal inversion 324 and can include a second portion of the middle segment 344 and some or all of the inner segment 346.

As illustrated in FIG. 3B, the braid 310 can be extended to a single-layer tubular shape during delivery. In the delivery shape, the coated sections 362, 364 can each respectively occupy separate, non-overlapping portions of the length L of the braid. The section 362 coated with cell adhesion coating can be positioned proximally in relation to the section 364 coated with anti-thrombogenic coating. Configured thusly, the section 364 coated with anti-thrombogenic coating can exit the catheter 30 into an aneurysm 10 (see FIG. 3C) prior to the section 362 coated with cell adhesion coating. Each respective coating can be disposed on the outer surface of the braid 310 when the braid is in the single-layer tubular shape.

As illustrated in FIG. 3C, the braid 310 can shape into an implanted shape. The implanted shape can be based on the predetermined shape illustrated in FIG. 3A and the anatomy of the aneurysm 10 illustrated in FIG. 3C. In the implanted shape, the braid 310 can have a proximal inversion 322a and a distal inversion 3224a corresponding to the proximal inversion 322 and the distal inversion 324 of the predetermined shape illustrated in FIG. 3A and three segments 342a, 344a, 346a corresponding to the three segments 342, 344, 346 illustrated in FIG. 3A. The middle segment 344a can have a compressed undulated sack within the aneurysm sac 12.

In the implanted shape, the section 364 coated with anti-thrombogenic coating can be positioned to occlude some or all of the aneurysm neck 16. The section 364 coated with anti-thrombogenic coating can form a barrier between the section 362 coated with cell adhesion coating and a parent blood vessel BV. The section 364 coated with anti-thrombogenic coating can inhibit blood clotting within the parent blood vessel BV near the aneurysm neck 16. A portion of the section 364 coated with anti-thrombogenic coating can be positioned to contact the aneurysm wall 14. The anti-thrombogenic coating can be disposed on a side of the braid 310 that is in communication with the parent blood vessel BV and in contact with the aneurysm wall 14.

In the implanted shape, the section 362 coated with cell adhesion coating can be contained within the aneurysm sac 12. The section 362 coated with cell adhesion coating can press the section 264 coated with anti-thrombogenic coating to the aneurysm wall 14. The section 362 coated with cell adhesion coating can induce thrombosis within the aneurysm sac 12. The cell adhesion coating can be disposed on a side of the braid 310 that is interior to the sack formed by the middle segment 344a.

In treatments in which the aneurysm 10 has a rupture near a distal portion 15 of the aneurysm wall 14, a portion of the section 362 with cell adhesion coating that is positioned across and/or near the rupture can be effective to form a clot over the rupture and thereby inhibit blood flow through the rupture. The implant 300 can thereby be effective to inhibit blood flow through such a rupture.

FIGS. 4A through 4C are illustrations of an implant 400 that can have a braid 410 having a predetermined shape as illustrated in FIG. 4A, a delivery shape as illustrated in FIG. 4B and an implanted shape as illustrated in FIG. 4C. FIGS. 4A and 4C illustrate the implant 400 in cross-section. The braid 410 can have a section 464 having an anti-thrombogenic coating and/or a section 462 having a cell adhesion coating. Two coated sections 462, 464 can be separated by an uncoated section 466.

As illustrated in FIG. 4A, the braid 410 can have two inversions 422, 424 and three segments 442, 444, 448. An outer segment 442 can extend between an open end 414 of the braid 410 and a proximal inversion 422. A middle segment 444 can extend between the proximal inversion 422 and a distal inversion 424. An inner segment 448 can extend between the distal inversion 424 and a pinched end 412 of the braid 410. The middle segment 444 can have a constriction 426.

In the predetermined shape, the section 464 coated with anti-thrombogenic coating can extend across the proximal inversion 422 and include some or all of the outer segment 442 and a first portion of the middle segment 444. The uncoated section 466 can extend across the constriction 426 and include a second portion of the middle segment 444. The section 462 coated with cell adhesion coating can extend across the distal inversion 424 and can include a third portion of the middle segment 444 and some or all of the inner segment 446.

As illustrated in FIG. 4B, the braid 410 can be extended to a single-layer tubular shape during delivery. In the delivery shape, the coated sections 462, 464 can each respectively occupy separate, non-overlapping portions of the length L of the braid. The section 462 coated with cell adhesion coating can be positioned proximally in relation to the section 464 coated with anti-thrombogenic coating. Configured thusly, the section 464 coated with anti-thrombogenic coating can exit the catheter 20 into an aneurysm 10 (see FIG. 4C) prior to the section 462 coated with cell adhesion coating. Each respective coating can be disposed on the outer surface of the braid 410 when the braid is in the single-layer tubular shape.

As illustrated in FIG. 4C, the braid 410 can shape into an implanted shape. The implanted shape can be based on the predetermined shape illustrated in FIG. 4A and the anatomy of the aneurysm 10 illustrated in FIG. 4C. In the implanted shape, the braid 410 can have a proximal inversion 422a and a distal inversion 424a corresponding to the proximal inversion 422 and the distal inversion 424 of the predetermined shape illustrated in FIG. 4A and three segments 442a, 444a, 446a corresponding to the three segments 442, 444, 446 illustrated in FIG. 4A. The middle segment 444a can form a sack within the aneurysm sac 12. The inner segment 446a can form a compaction resistant post within the aneurysm sac 12.

In the implanted shape, the section 464 coated with anti-thrombogenic coating can be positioned to occlude some or all of the aneurysm neck 16. The section 464 coated with anti-thrombogenic coating can form a barrier between the section 462 coated with cell adhesion coating and a parent blood vessel BV. The section 464 coated with anti-thrombogenic coating can inhibit blood clotting within the parent blood vessel BV near the aneurysm neck 16. A portion of the section 464 coated with anti-thrombogenic coating can be positioned to contact the aneurysm wall 14. The anti-thrombogenic coating can be disposed on a side of the braid 410 that is in communication with the parent blood vessel BV and in contact with the aneurysm wall 14.

In the implanted shape, the section 462 coated with cell adhesion coating can be contained within the aneurysm sac 12. The section 462 coated with cell adhesion coating can press the section 464 coated with anti-thrombogenic coating to the aneurysm wall 14. The section 462 coated with cell adhesion coating can induce thrombosis within the aneurysm sac 12. The cell adhesion coating can be disposed on a side of the braid 410 that is interior to the sack formed by the middle segment 444a and on an outer surface of the compaction resistant post 446a.

In the implanted shape, the uncoated section 466 can be positioned near the center of the aneurysm neck 16.

In treatments in which the aneurysm 10 has a rupture near a distal portion 15 of the aneurysm wall 14, a portion of the section 462 with cell adhesion coating that is positioned across and/or near the rupture can be effective to form a clot over the rupture and thereby inhibit blood flow through the rupture. The implant 400 can thereby be effective to inhibit blood flow through such a rupture.

As an alternative to coating the entire portion of the braid 410 corresponding to the outer segment 442 of the braid 110 in the predetermined shape illustrated in FIG. 4A with an anti-thrombogenic coating, a portion of the braid 410 extending from the open end 414 to approximately mid-way through the outer segment 442 can be coated with a cell adhesion coating and the remainder of the outer segment 442 can be coated with an anti-thrombogenic coating. In this way, when implanted, a portion of the outer sack 442a contained completely within the aneurysm can be coated with a cell adhesion coating and the entire portion of the outer sack 442a exposed to the blood vessel BV can be coated with anti-thrombogenic coating. The additional section coated with cell adhesion coating can, in some applications, increase the speed at which thrombus forms in the aneurysm 10 and improve the effectiveness of the implant 400 at healing a rupture.

FIGS. 5A through 5C are illustrations of an implant 500 having a braid 510 having a predetermined shape as illustrated in FIG. 5A, a delivery shape as illustrated in FIG. 5B, and an implanted shape as illustrated in FIG. 5C similar to corresponding shapes disclosed in U.S. patent application Ser. No. 15/989,725 incorporated herein by reference. The braid 510 can have a section 564 having an anti-thrombogenic coating and/or a section 562 having a cell adhesion coating. Two coated sections 562, 564 can be separated by an uncoated section 566.

As illustrated in FIG. 5A, in the predetermined shape, the braid 510 can have a distal sack 544 extending from a distal end 514 of the braid, a proximal bowl 542 extending from a proximal end 512 of the braid 510, and a constriction 526 between the distal sack 544 and proximal bowl 542. The section 564 coated with anti-thrombogenic coating can include some or all of the proximal bowl 542. The uncoated section 566 can extend across the constriction 526. The section 562 coated with cell adhesion coating can include some or all of the distal sack 544.

As illustrated in FIG. 5B, the braid 510 can be extended to a single-layer tubular shape during delivery. In the delivery shape, the coated sections 562, 564 can each respectively occupy separate, non-overlapping portions of the length L of the braid. The section 562 coated with cell adhesion coating can be positioned distally in relation to the section 564 coated with anti-thrombogenic coating. Configured thusly, the section 562 coated with cell adhesion coating can exit the catheter 20 into an aneurysm 10 (see FIG. 5C) prior to the section 564 coated with anti-thrombogenic coating. Each respective coating can be disposed on the outer surface of the braid 510 when the braid is in the single-layer tubular shape. Additionally, or alternatively, cell adhesion coating can be disposed on the inner surface of the braid 510 when the braid is in the single-layer tubular shape.

As illustrated in FIG. 5C, the braid 510 can shape into an implanted shape. The implanted shape can be based on the predetermined shape illustrated in FIG. 5A and the anatomy of the aneurysm 10 illustrated in FIG. 5C. In the implanted shape, the braid 510 can have a bowl 542a corresponding to the bowl 542 of the predetermined shape illustrated in FIG. 5A and a distal sack 544a corresponding to the distal sack 544 illustrated in FIG. 5A.

In the implanted shape, the section 564 coated with anti-thrombogenic coating can be positioned to occlude some or all of the aneurysm neck 16. The section 564 coated with anti-thrombogenic coating can form a barrier between the section 562 coated with cell adhesion coating and a parent blood vessel BV. The section 564 coated with anti-thrombogenic coating can inhibit blood clotting within the parent blood vessel BV near the aneurysm neck 16. A portion of the section 564 coated with anti-thrombogenic coating can be positioned to contact the aneurysm wall 14. The anti-thrombogenic coating can be disposed on a side of the braid 510 that is in communication with the parent blood vessel BV and in contact with the aneurysm wall 14.

In the implanted shape, the section 562 coated with cell adhesion coating can be contained within the aneurysm sac 12. The section 562 coated with cell adhesion coating can press the section 564 coated with anti-thrombogenic coating to the aneurysm wall 14. The section 562 coated with cell adhesion coating can induce thrombosis within the aneurysm sac 12. The cell adhesion coating can be disposed on a side of the braid 510 that is exterior to the distal sack 544a. Additionally, or alternatively, cell adhesion coating can be disposed on a surface that is interior to the distal sack 544a. Preferably, the cell adhesion coating can be disposed on the surface interior to the distal sack 544a.

In treatments in which the aneurysm 10 has a rupture near a distal portion 15 of the aneurysm wall 14, a portion of the section 562 with cell adhesion coating that is positioned across and/or near the rupture can be effective to form a clot over the rupture and thereby inhibit blood flow through the rupture. The implant 500 can thereby be effective to inhibit blood flow through such a rupture.

In the implanted shape, the uncoated section 566 can be positioned centrally within the aneurysm sac 12.

FIGS. 6A through 6C are illustrations of an implant 600 having braid 610 having a predetermined shape as illustrated in FIG. 6A, a delivery shape as illustrated in FIG. 6B, and an implanted shape as illustrated in FIG. 6C similar to corresponding shapes disclosed in U.S. patent application Ser. No. 15/852,829 incorporated herein by reference. The braid 610 can have a section 664 having an anti-thrombogenic coating and/or a section 662 having a cell adhesion coating. The braid 610 can include a constricted section 626. The constricted section 626 can be positioned between the cell adhesion coated section 662 and the anti-thrombogenic coated section 664. The implant 100 can further include band 670 constricting the braid 610 at the constricted section. Although not illustrated, the braid 610 can include an uncoated section.

The implant 600 can be constructed from a braid 610 that can be shaped into a single layer tube having a first end 614 and a second end 612. When the braid 610 is extended as such, each of the respective coated sections 662, 664 can be positioned such that they are non-overlapping, occupying separate portions of the length of the braid 610. In some examples, the band 670 can be positioned at or near a boundary between the coated sections 662, 664 or between the two coated sections 662, 664. In some examples, the band 670 can be positioned over the section 664 coated with anti-thrombogenic coating.

As illustrated in FIG. 6A, in the predetermined shape, the braid 610 can have an inner sack 644 extending between one end 614 of the braid 610 and the band 670 and an outer sack 642 extending between the other end 612 of the braid 610 and the band 670. The outer sack 642 is illustrated in cross-section. The section 664 coated with anti-thrombogenic coating can include some or all of the outer sack 642. The section 662 coated with cell adhesion coating can include some or all of the inner sack 644.

As illustrated in FIG. 6B, the braid 610 can be collapsed for delivery through a catheter 20. In the delivery shape, the braid 610 can be inverted near the band 670 such that the section 664 coated with anti-thrombogenic coating can surround at least a portion of the section 662 coated with cell adhesion coating. Inverted as such, the outer surface of the section 664 coated with anti-thrombogenic coating can correspond to an inner surface of the braid 610 with the braid 610 is in a single-layer tubular shape, and the inner surface of the section 662 coated with cell adhesion coating can correspond to an inner surface of the braid 610 when the braid 610 is in the single-layer tubular shape. The anti-thrombogenic coating can be applied to the outer surface of the corresponding section 664. The cell adhesion coating can be applied to the inner surface of the corresponding section 622.

As illustrated in FIG. 6C, the braid 610 can shape into an implanted shape. The implanted shape can be based on the predetermined shape illustrated in FIG. 6A and the anatomy of the aneurysm 10 illustrated in FIG. 6C. In the implanted shape, the braid 610 can have an outer sack 642a corresponding to the outer sack 642 of the predetermined shape illustrated in FIG. 6A and an inner sack 644a corresponding to the inner sack 644 illustrated in FIG. 6A. The outer sack 642a is illustrated in cross-section.

In the implanted shape, the section 664 coated with anti-thrombogenic coating can be positioned to occlude some or all of the aneurysm neck 16. The section 664 coated with anti-thrombogenic coating can form a barrier between the section 662 coated with cell adhesion coating and a parent blood vessel BV. The section 664 coated with anti-thrombogenic coating can inhibit blood clotting within the parent blood vessel BV near the aneurysm neck 16. A portion of the section 664 coated with anti-thrombogenic coating can be positioned to contact the aneurysm wall 14. The anti-thrombogenic coating can be disposed on a side of the braid 610 that is in communication with the parent blood vessel BV and in contact with the aneurysm wall 14.

In the implanted shape, the section 662 coated with cell adhesion coating can be contained within the aneurysm sac 12. The section 662 coated with cell adhesion coating can press the section 664 coated with anti-thrombogenic coating to the aneurysm wall 14. The section 662 coated with cell adhesion coating can induce thrombosis within the aneurysm sac 12. The cell adhesion coating can be disposed on a side of the braid 610 interior to the inner sack 644a.

In treatments in which the aneurysm 10 has a rupture near a distal portion 15 of the aneurysm wall 14, a portion of the section 662 with cell adhesion coating that is positioned across and/or near the rupture can be effective to form a clot over the rupture and thereby inhibit blood flow through the rupture. The implant 600 can thereby be effective to inhibit blood flow through such a rupture.

FIGS. 7A through 7C are illustrations of an implant 700 having a braid 710 having a predetermined shape as illustrated in FIG. 7A, a delivery shape as illustrated in FIG. 7B, and an implanted shape as illustrated in FIG. 7C similar to corresponding shapes disclosed in U.S. patent application Ser. No. 15/993,903 incorporated herein by reference. The braid 710 can have a section 764 having an anti-thrombogenic coating and/or a section 762 having a cell adhesion coating. Two coated sections 762, 764 can be separated by an uncoated section 766.

As illustrated in FIG. 7A, in the predetermined shape, the braid 710 can have a distal sack 746 extending from a distal end 714 of the braid to a distal inflection point 724, a central segment 744 extending from the distal inflection point 724 to a proximal inflection point 722, and a proximal segment 742 extending between the proximal inflection point 722 and the proximal end 712 of the braid 710. The section 764 coated with anti-thrombogenic coating can span the distal inflection point 724, include some or all of the distal sack 746 and a portion of the central segment 744. The uncoated section 766 can extend within the central segment 744. The section 762 coated with cell adhesion coating can span the proximal inflection point 722 and include some or all of the proximal segment 742 and a portion of the central segment 744.

As illustrated in FIG. 7B, the braid 710 can be extended to a single-layer tubular shape during delivery. In the delivery shape, the coated sections 762, 764 can each respectively occupy separate, non-overlapping portions of the length L of the braid. The section 762 coated with cell adhesion coating can be positioned proximally in relation to the section 764 coated with anti-thrombogenic coating. Configured thusly, the section 764 coated with anti-thrombogenic coating can exit the catheter 20 into an aneurysm 10 (see FIG. 5C) prior to the section 762 coated with cell adhesion coating. Each respective coating can be disposed on the outer surface of the braid 710 when the braid is in the single-layer tubular shape. Additionally, or alternatively, the cell adhesion coating can be applied on an inner surface of the braid 710 when the braid is in the single-layer tubular shape.

As illustrated in FIG. 7C, the braid 710 can shape into an implanted shape. The implanted shape can be based on the predetermined shape illustrated in FIG. 7A and the anatomy of the aneurysm 10 illustrated in FIG. 7C. In the implanted shape, the braid 710 can have a sack 746a corresponding to the distal sack 746 of the predetermined shape illustrated in FIG. 7A, an inversion 724a near the aneurysm neck 16 corresponding to the distal inflection point 724 in the predetermined shape, and an intrasaccular inversion 722a corresponding to the proximal inflection point 722 in the predetermined shape. Portions of the braid 710 corresponding to the central segment 744 and the proximal segment 742 in the predetermined shape can be contained within the sack 746a in the implanted shape.

In the implanted shape, the section 764 coated with anti-thrombogenic coating can be positioned to occlude some or all of the aneurysm neck 16. The section 764 coated with anti-thrombogenic coating can form a barrier between the section 762 coated with cell adhesion coating and a parent blood vessel BV. The section 764 coated with anti-thrombogenic coating can inhibit blood clotting within the parent blood vessel BV near the aneurysm neck 16. A portion of the section 764 coated with anti-thrombogenic coating can be positioned to contact the aneurysm wall 14. The anti-thrombogenic coating can be disposed on a side of the braid 710 that is in communication with the parent blood vessel BV and in contact with the aneurysm wall 14.

In the implanted shape, the section 762 coated with cell adhesion coating can be contained within the aneurysm sac 12. The section 762 coated with cell adhesion coating can induce thrombosis within the aneurysm sac 12. The cell adhesion coating can be disposed on a side of the braid 510 that is between the central segment 744 and proximal segment 742. Additionally, or alternatively, the cell adhesion coating can be disposed on the opposite side of the braid.

In the implanted shape, the uncoated section 766 can be positioned near the center of the aneurysm neck 16.

FIGS. 8A through 8C are illustrations of an implant 800 having a braid 810 having a predetermined shape as illustrated in FIG. 8A, a delivery shape as illustrated in FIG. 8B, and an implanted shape as illustrated in FIG. 8C similar to corresponding shapes disclosed in U.S. patent application Ser. No. 16/159,582 incorporated herein by reference. The braid 810 is illustrated in cross-section in FIG. 8C. The braid 810 can have a section 864 having an anti-thrombogenic coating and/or a section 862 having a cell adhesion coating. Two coated sections 862, 864 can be separated by an uncoated section 866. The implant 800 can further include bands 832, 834 constricting the ends 812, 814 of the braid 810.

As illustrated in FIG. 8A, in the predetermined shape, the braid 810 can have an outer sack 842, an inner sack 844, and a fold 822 separating the sacks 842, 844. The section 864 coated with anti-thrombogenic coating can include some or all of the outer sack 842. The uncoated section 866 can extend across the fold 822. The section 862 coated with cell adhesion coating can include some or all of the inner sack 844. Alternatively, the section 862 coated with cell adhesion coating can include some or all of the inner sack 844, extend across the fold 822, and include a portion of the outer sack 842.

As illustrated in FIG. 8B, the braid 810 can be extended to a single-layer tubular shape during delivery. In the delivery shape, the coated sections 862, 864 can each respectively occupy separate, non-overlapping portions of the length L of the braid. The section 862 coated with cell adhesion coating can be positioned distally in relation to the section 864 coated with anti-thrombogenic coating. Configured thusly, the section 862 coated with cell adhesion coating can exit the catheter 20 into an aneurysm 10 (see FIG. 8C) prior to the section 862 coated with anti-thrombogenic coating. Each respective coating can be disposed on the outer surface of the braid 810 when the braid is in the single-layer tubular shape.

As illustrated in FIG. 8C, the braid 810 can shape into an implanted shape. The implanted shape can be based on the predetermined shape illustrated in FIG. 8A and the anatomy of the aneurysm 10 illustrated in FIG. 8C. In the implanted shape, the braid 810 can have an outer sack 842a corresponding to the outer sack 842 of the predetermined shape illustrated in FIG. 8A, an inner sack 844a corresponding to the inner sack 844 illustrated in FIG. 8A, and a fold 822a corresponding to the fold 822 illustrated in FIG. 8A.

In the implanted shape, the section 864 coated with anti-thrombogenic coating can be positioned to occlude some or all of the aneurysm neck 16. The section 864 coated with anti-thrombogenic coating can form a barrier between the section 862 coated with cell adhesion coating and a parent blood vessel BV. The section 864 coated with anti-thrombogenic coating can inhibit blood clotting within the parent blood vessel BV near the aneurysm neck 16. A portion of the section 864 coated with anti-thrombogenic coating can be positioned to contact the aneurysm wall 14. The anti-thrombogenic coating can be disposed on a side of the braid 810 that is in communication with the parent blood vessel BV and in contact with the aneurysm wall 14.

In the implanted shape, the section 862 coated with cell adhesion coating can be contained within the aneurysm sac 12. The section 862 coated with cell adhesion coating can press the section 864 coated with anti-thrombogenic coating to the aneurysm wall 14. The section 862 coated with cell adhesion coating can induce thrombosis within the aneurysm sac 12. The cell adhesion coating can be disposed on a side of the braid 810 that is interior to the inner sack 844a. Additionally, the cell adhesion coating can be disposed on portion of the braid and on a side of the braid 810 that is in contact with the aneurysm wall 14.

In the implanted shape, the uncoated section 866 can be positioned along a ridge defined by the fold 822a. Alternatively, the uncoated section 866 can be positioned to contact the aneurysm wall 14 and the section 864 coated with anti-thrombogenic coating can include the fold 822a. In another alternative, the implant 800 need not include an uncoated section.

FIGS. 9A through 9D are illustrations of an implant 900 having a braid 910 having a predetermined shape as illustrated in FIG. 9A, two delivery shapes as illustrated in FIGS. 9B and 9C, and an implanted shape as illustrated in FIG. 9D similar to corresponding shapes disclosed in U.S. patent application Ser. No. 16/366,235 incorporated herein by reference. The braid 910 can have a section 964 having an anti-thrombogenic coating and/or a section 962 having a cell adhesion coating. Two coated sections 962, 964 can be separated by an uncoated section 966.

As illustrated in FIG. 9A, in the predetermined shape, the braid 910 can have a sack 944, an elongated portion 942, and an inversion 922 separating the sack 944 and elongated portion 942. The sack 944 is illustrated in cross-section. The section 964 coated with anti-thrombogenic coating can include some or all of the sack 944. The uncoated section 966 can be positioned as a band across the sack 944. Additionally, or alternatively, the uncoated section can extend across the inversion 922. The section 962 coated with cell adhesion coating can include some or all of the elongated portion 942. The section 962 coated with cell adhesion coating can extend across the inversion 922 and include a portion of the sack 944 in addition to some or all of the elongated portion 942.

It is also contemplated that the implant 900 can include an embolic coil in addition to and/or in place of the elongated portion 942 illustrated in FIG. 9A and the corresponding segments 942a, 942b of the braid 910 in the delivery and implanted shapes illustrated in FIGS. 9B through 9D. In such an example, the braid 910 can include the sack 944, and the sack 944 can include one or more coated sections 962, 964 as described and illustrated.

As illustrated in FIG. 9B, the braid 910 can be extended to a single-layer tubular shape during delivery. In the delivery shape, the coated sections 962, 964 can each respectively occupy separate, non-overlapping portions of the length L of the braid. The section 962 coated with cell adhesion coating can be positioned proximally in relation to the section 964 coated with anti-thrombogenic coating. Configured thusly, the section 964 coated with anti-thrombogenic coating can exit the catheter 20 into an aneurysm 10 (see FIG. 9D) prior to the section 962 coated with cell adhesion coating. The anti-thrombogenic coating can be disposed on the inner surface, within the lumen, of the braid 910. The cell adhesion coating can be disposed on the outer surface of the braid 910.

As illustrated in FIG. 9C, the braid can be folded approximate the inversion 922 in the predetermined shape to form a fold 922a in the delivery shape. In the delivery shape, the braid 910 can have an outer segment 944a corresponding to the sack 944 in the predetermined shape that surrounds an elongated portion 942a corresponding to the elongated portion 942 in the predetermined shape. Inverted as such, a portion of the inner surface of the lumen of the braid when the braid is extended to a single layer tube is the outer surface of the outer segment 994a when the braid 910 is in the delivery configuration illustrated in FIG. 9C. The anti-thrombogenic coating can be disposed on the outer surface of the outer segment 944a. The cell adhesion coating can be disposed on the outer surface of the elongated portion 942a.

As illustrated in FIG. 9D, the braid 910 can shape into an implanted shape. The implanted shape can be based on the predetermined shape illustrated in FIG. 9A and the anatomy of the aneurysm 10 illustrated in FIG. 9D. In the implanted shape, the braid 910 can have a sack 944b corresponding to the outer sack 944 of the predetermined shape illustrated in FIG. 9A, a looping portion 942b corresponding to the elongated portion 942 illustrated in FIG. 9A, and an inversion 922b corresponding to the inversion 922 illustrated in FIG. 9A.

In the implanted shape, the section 964 coated with anti-thrombogenic coating can be positioned to occlude some or all of the aneurysm neck 16. The section 964 coated with anti-thrombogenic coating can form a barrier between the section 962 coated with cell adhesion coating and a parent blood vessel BV. The section 964 coated with anti-thrombogenic coating can inhibit blood clotting within the parent blood vessel BV near the aneurysm neck 16. A portion of the section 964 coated with anti-thrombogenic coating can be positioned to contact the aneurysm wall 14. The anti-thrombogenic coating can be disposed on a side of the braid 910 that is in communication with the parent blood vessel BV and in contact with the aneurysm wall 14.

In the implanted shape, the section 962 coated with cell adhesion coating can be contained within the aneurysm sac 12. The section 962 coated with cell adhesion coating can press the section 964 coated with anti-thrombogenic coating to the aneurysm wall 14. The section 962 coated with cell adhesion coating can induce thrombosis within the aneurysm sac 12. The cell adhesion coating can be disposed on a side of the braid 910 that is on the outside of the looping portion 942b.

In treatments in which the aneurysm 10 has a rupture near a distal portion 15 of the aneurysm wall 14, a portion of the section 962 with cell adhesion coating that is positioned across and/or near the rupture can be effective to form a clot over the rupture and thereby inhibit blood flow through the rupture. The implant 900 can thereby be effective to inhibit blood flow through such a rupture.

In the implanted shape, the uncoated section 966 can be positioned to form a band in the sack 944b and positioned to contact the aneurysm wall 14. Alternatively, the uncoated section 966 can be positioned to extend across the inversion 922b and be positioned near the distal portion 15 of the aneurysm wall 14. Alternatively, the implant 900 need not include an uncoated section.

FIGS. 10A through 10C are illustrations of an implant 1000 having a braid 1010 having a predetermined shape as illustrated in FIG. 10A, a delivery shape as illustrated in FIG. 10B, and an implanted shape as illustrated in FIG. 10C similar to corresponding shapes disclosed in U.S. patent application Ser. No. 16/366,115 incorporated herein by reference. The braid 1010 can have a section 1064 having an anti-thrombogenic coating and/or a section 1062 having a cell adhesion coating. The implant 1000 can include a closure mechanism or constriction band 1026. The constriction band 1026 can be positioned between the two coated sections 1062, 1064.

As illustrated in FIG. 10A, in the predetermined shape, the braid 1010 can have an occluding portion 1044 and an elongated portion 1042. The section 1064 coated with anti-thrombogenic coating can include some or all of the occluding portion 1044. The section 1062 coated with cell adhesion coating can include some or all of the elongated portion 1042.

The implant 1000 can be constructed from a braid 1010 that can be shaped into a single layer tube having a first end 1014 and a second end 1012. When the braid 1010 is extended as such, each of the respective coated sections 1062, 1064 can be positioned such that they are non-overlapping, occupying separate portions of the length of the braid 1010. The band 1026 can be positioned at or near a boundary between the coated sections 1062, 1064 or between the two coated sections 1062, 1064.

It is also contemplated that the implant 1000 can include an embolic coil in addition to and/or in place of the elongated portion 1042 illustrated in FIG. 10A and the corresponding segments 1042a, 1042b of the braid 1010 in the delivery and implanted shapes illustrated in FIGS. 10B and 10C. In such an example, the braid 1010 can include the occluding portion 1044, and the occluding portion 1044 can include the anti-thrombogenic coated section 1062 as illustrated.

As illustrated in FIG. 10B, the braid 1010 can be folded approximate the band 1026 such that the occluding portion 1044 in the predetermined shape forms an outer segment 1044*a* in the delivery shape. The outer segment 1044*a* is illustrated in cross-section. The outer segment 1044*a* can be positioned to surround an elongated portion 1042*a* corresponding to the elongated portion 1042 in the predetermined shape. Inverted as such, a portion of the inner surface of the lumen of the braid when the braid is extended to a single layer tube is the outer surface of the outer segment 1044*a* when the braid 1010 is in the delivery configuration illustrated in FIG. 10B. The anti-thrombogenic coating can be disposed on the outer surface of the outer segment 1044*a*. The cell adhesion coating can be disposed on the outer surface of the elongated portion 1042*a*.

As illustrated in FIG. 10C, the braid 1010 can shape into an implanted shape. The implanted shape can be based on the predetermined shape illustrated in FIG. 10A and the anatomy of the aneurysm 10 illustrated in FIG. 10C. In the implanted shape, the braid 1010 can have an occluding portion 1044*b* corresponding to the occluding portion 1044 of the predetermined shape illustrated in FIG. 10A and a looping portion 1042*b* corresponding to the elongated portion 1042 illustrated in FIG. 10A.

In the implanted shape, the section 1064 coated with anti-thrombogenic coating can be positioned to occlude some or all of the aneurysm neck 16. The section 1064 coated with anti-thrombogenic coating can form a barrier between the section 1062 coated with cell adhesion coating and a parent blood vessel BV. The section 1064 coated with anti-thrombogenic coating can inhibit blood clotting within the parent blood vessel BV near the aneurysm neck 16. A portion of the section 1064 coated with anti-thrombogenic coating can be positioned to contact the aneurysm wall 14. The anti-thrombogenic coating can be disposed on a side of the braid 1010 that is in communication with the parent blood vessel BV and in contact with the aneurysm wall 14.

In the implanted shape, the section 1062 coated with cell adhesion coating can be contained within the aneurysm sac 12. The section 1062 coated with cell adhesion coating can press the section 1064 coated with anti-thrombogenic coating to the aneurysm wall 14. The section 1062 coated with cell adhesion coating can induce thrombosis within the aneurysm sac 12. The cell adhesion coating can be disposed on a side of the braid 1010 that is on the outside of the looping portion 1042*b*. It is also contemplated that an embolic coil used in addition to or in place of the looping portion 1042*a* can press the section 1064 coated with cell adhesion coating to the aneurysm wall 14.

In treatments in which the aneurysm 10 has a rupture near a distal portion 15 of the aneurysm wall 14, a portion of the section 1062 with cell adhesion coating that is positioned across and/or near the rupture can be effective to form a clot over the rupture and thereby inhibit blood flow through the rupture. The implant 1000 can thereby be effective to inhibit blood flow through such a rupture.

FIGS. 11A through 11C are illustrations of an implant 1100 having a braid 1110 having a predetermined shape as illustrated in FIG. 11A, a delivery shape as illustrated in FIG. 11B, and an implanted shape as illustrated in FIG. 11C. The braid 1110 can have a section 1164 having an anti-thrombogenic coating and/or a section 1162 having a cell adhesion coating. The implant 1100 can include a closure mechanism or constriction band 1126. The constriction band 1126 can be positioned between the two coated sections 1162, 1164.

As illustrated in FIG. 11A, in the predetermined shape, the braid 1110 can have a single layer bowl shape.

The implant 1100 can be constructed from a braid 1110 that can be shaped into a single layer tube having a first end 1114 and a second end 1112 as illustrated in FIG. 11B. When the braid 1110 is extended as such, each of the respective coated sections 1162, 1164 can be positioned such that they are non-overlapping, occupying separate portions of the length of the braid 1110. The band 1126 can be positioned at or near a boundary between the coated sections 1162, 1164 or between the two coated sections 1162, 1164. Positioned as such, the braid 1110 can be delivered through a catheter 20 to an aneurysm 10. The cell adhesion coated section 1162 can extend from the distal end 1114 and the anti-thrombogenic section 1164 can extend from the proximal end 1112.

As illustrated in FIG. 11C, the braid 1110 can shape into an implanted shape. The implanted shape can be based on the predetermined shape illustrated in FIG. 11A and the anatomy of the aneurysm 10 illustrated in FIG. 11C. In the implanted shape, the braid 1110 can have a substantially spherical shape.

In the implanted shape, the section 1164 coated with anti-thrombogenic coating can be positioned to occlude some or all of the aneurysm neck 16. The section 1164 coated with anti-thrombogenic coating can form a barrier between the section 1162 coated with cell adhesion coating and a parent blood vessel BV. The section 1164 coated with anti-thrombogenic coating can inhibit blood clotting within the parent blood vessel BV near the aneurysm neck 16. A portion of the section 1164 coated with anti-thrombogenic coating can be positioned to contact the aneurysm wall 14. The anti-thrombogenic coating can be disposed on a side of the braid 1110 that is in communication with the parent blood vessel BV and in contact with the aneurysm wall 14.

In the implanted shape, the section 1162 coated with cell adhesion coating can be contained within the aneurysm sac 12. The section 1162 coated with cell adhesion coating can press the section 1164 coated with anti-thrombogenic coating to the aneurysm wall 14. The section 1162 coated with cell adhesion coating can induce thrombosis within the aneurysm sac 12.

In treatments in which the aneurysm 10 has a rupture near a distal portion 15 of the aneurysm wall 14, a portion of the section 1162 with cell adhesion coating that is positioned across and/or near the rupture can be effective to form a clot over the rupture and thereby inhibit blood flow through the rupture. The implant 1100 can thereby be effective to inhibit blood flow through such a rupture.

FIG. 12 is a flow diagram outlining example method steps for designing, constructing, or configuring an implant and/or system. The method steps can be implemented to design, construct, or configure example implants and systems presented herein, variations thereof, and alternative implant and systems as would be appreciated and understood by a person of ordinary skill in the art.

Referring to method 1200 outlined in FIG. 12, in step 1210, a tubular braided mesh can be selected. Preferably, the tubular braided mesh can have, be constructed from, and/or be movable to a single-layer tube shape. The tubular braided mesh need not be in the shape of the a single-layer tube when selected, and can be inverted, expanded, looped, folded, or otherwise shaped.

In step 1220, two non-overlapping sections of the tubular braided mesh can be coated. The coating can be applied with spray coating, dip coating, or by other means described herein and/or as would be appreciated and understood by a person of ordinary skill in the art. In some examples, one or both of each respective coating can be applied to only one of an inner surface or an outer surface of the braid. In some examples, one or both of each respective coating can be applied to both an inner surface and an outer surface of the braid. In some examples, one coating can be applied to an inner surface of the braid and not an outer surface of the braid and the other coating can be applied to an outer surface of the braid and not an inner surface of the braid such that the inner surfaces and the outer surfaces are defined by the inner (intralumenal) and outer surfaces of the braid when the braid is in a single-layer, non-inverted configuration.

In step 1230, the braided mesh can be shaped into a predetermined shape sized to be placed within an aneurysm. The predetermined shape can be sized such that the implant is configured for treating a predetermined range of aneurysm sizes. The predetermined shape can be sized such that when implanted the braid conforms to an implanted shape effective to anchor within an aneurysm sac. The predetermined shape can be a predetermined shape as described herein, a variation thereof, or a predetermined shape as otherwise appreciated and understood by a person of ordinary skill in the art.

In step 1240, a delivery system locking portion/detachment feature can be attached to the braided mesh. The detachment feature can be attached to the braided mesh such that the detachment feature remains attached to the braided mesh when the implant is implanted. The detachment feature can be configured to detachably attached to a delivery system and/or otherwise be configured to engage a delivery system during delivery of the implant and disengage the delivery system once the implant is in an implanted position.

In step 1250, the braided mesh can be collapsed to fit within a catheter. The braided mesh can be collapsed to a delivery shape as described herein, variations thereof, or alternative delivery shape as would be appreciated and understood by a person of ordinary skill in the art.

FIG. 13 is a flow diagram outlining example method steps for treating an aneurysm with an implant and/or system such as an example implant and/or system described herein, variations thereof, or alternative implant and/or system as would be appreciated and understood by a person ordinary skill in the art.

Referring to method 1300 outlined in FIG. 13, in step 1310 a braided implant suitable for treating an aneurysm can be selected. The selected implant can include an example implant described herein, a variation thereof, or an alternative implant as would be appreciated and understood by a person of ordinary skill in the art.

In step 1320, the implant can be collapsed to fit within a catheter. The implant can be collapsed to a delivery shape as described herein, a variation thereof, or an alternative as would be appreciated and understood by a person of ordinary skill in the art.

In step 1330, the implant can be delivered through the catheter to the aneurysm. During delivery, the implant can be positioned within the catheter in an orientation described herein, a variation thereof, or an alternative orientation as would be appreciated and understood by a person of ordinary skill in the art.

In step 1340, a portion of the braid coated with an anti-thrombogenic coating can be positioned to occlude some or all of the aneurysm's neck.

In step 1350, a portion of the braid coated with cell adhesion coating can be positioned in the aneurysm's sac.

The portion of the braid coated with cell adhesion coating can form an expanded shape such as a sack, bowl, or other expanded shape. Additionally, or alternatively, the braid coated with cell adhesion coating can loop within the aneurysm's sac. The portion of the braid coated with cell adhesion coating can be positioned to press into the aneurysm wall and anchor the implant within the aneurysm's sac.

In step 1360, the anti-thrombogenic coating can inhibit blood clotting in a parent blood vessel adjacent the aneurysm. The anti-thrombogenic coating can inhibit blood clot formation within the parent blood vessel on a portion of the braid extending within the parent blood vessel when implanted.

In step 1370, the cell adhesion coating can promote blood clotting within the aneurysm. In an implant having a rupture, the blood clotting can be effective to inhibit blood flow through the rupture.

The descriptions contained herein are examples of embodiments of the invention and are not intended in any way to limit the scope of the invention. As described herein, the invention contemplates many variations and modifications of the implants, including alternative braid shapes, alternative coating placements, alternative materials, alternative delivery system engagement/detachment features, alternative braid size, alternative braid porosity, alternative methods for applying a coating to a braid, additional intrasaccular implant structures such as struts or anchors, alternative braid materials, alternative surface enhancement techniques to achieve enhanced cell adhesion to the braid, alternative surface enhancement techniques to achieve enhanced anti-thrombogenic properties of the braid, etc. These modifications would be apparent to those having ordinary skill in the art to which this invention relates and are intended to be within the scope of the claims which follow.

What is claimed is:
1. An implant comprising:
a braided mesh movable from a delivery configuration having a single-layer tubular shape sized to traverse a catheter to an implanted configuration sized to be implanted in an aneurysm sac, the braided mesh having a length;
an anti-thrombogenic coating disposed on the braided mesh defining a first section along the length of the braided mesh in the delivery configuration, the first section having a first end and a second end; and
a cell adhesion coating disposed on the braided mesh defining a second section along the length of the braided mesh in the delivery configuration, the second section having a first end and a second end, both the first end and the second end located proximally of the first section in the delivery configuration,
wherein the second end of the second section is joined to an uncoated section that is joined to the first end of the first section,
wherein, in the implanted configuration, the first section forms at least part of an outer segment and the second section forms at least part of an inner segment,
wherein the braided mesh is configured such that the second section is invertible to the implanted configuration causing the uncoated section, the first end of the second section, and the second end of the second section to be aligned distal to the first end of the first section, and
wherein, when the braided mesh is in the implanted configuration, the second section is positioned within the aneurysm sac and the first section is positioned to occlude an aneurysm neck.

2. The implant of claim 1, wherein, when the braided mesh is in the implanted configuration, the first section is positioned to form a barrier between the second section and a parent blood vessel.

3. The implant of claim 1, wherein, when the braided mesh is in the implanted configuration, the second section forms a sack within the aneurysm sac.

4. The implant of claim 1, wherein, when the braided mesh is in the implanted configuration, the first section is positioned to contact an aneurysm wall and the second section is positioned to press the first section against the aneurysm wall.

5. The implant of claim 1, wherein:
when the braided mesh is in the delivery configuration, the first section is disposed distal to the second section and toward the aneurysm sac; and
when the braided mesh is in the implanted configuration, the first section is positioned to contact an aneurysm wall and the second section is positioned to press the first section against the aneurysm wall.

6. The implant of claim 1, wherein:
when the braided mesh is in the delivery configuration, the first section is disposed distal to the second section and toward the aneurysm sac; and
when the braided mesh is in the implanted configuration, the first section surrounds at least a portion of the second section.

7. The implant of claim 1, further comprising a lock connectable to a delivery system and positioned proximate a first end of the second section,
wherein, when the braided mesh is in the delivery configuration:
the first section is disposed distal to the second section and toward the aneurysm sac;
the first section is disposed at a second end of the second section; and
the second section is disposed between the lock and the first section.

8. The implant of claim 7, wherein, when the braided mesh is in the implanted configuration, the lock is positioned distal to the first section.

9. The implant of claim 1, wherein, when the braided mesh is in the implanted configuration, the first section and the second section are contained completely within the aneurysm sac.

10. A method of implanting the implant of claim 1 comprising:
positioning the first section of the braided mesh coated with the anti-thrombogenic coating to occlude the aneurysm neck; and
positioning the second section of the braided mesh coated with the cell adhesion coating within the aneurysm sac.

11. The method of claim 10, further comprising:
obstructing, with the first section, communication between the cell adhesion coating and a parent blood vessel of an aneurysm.

12. The method of claim 10, further comprising:
collapsing the braided mesh into the delivery configuration; and
positioning the braided mesh, in the delivery configuration, into the catheter such that the first section is positioned distally in relation to the second section.

13. The method of claim 10, further comprising:
positioning the first section to contact an aneurysm wall; and
positioning the second section to press the first section to the aneurysm wall.

14. The method of claim 10, further comprising:
collapsing the braided mesh into the delivery configuration;
positioning the braided mesh, in the delivery configuration, within the catheter such that the first section is positioned distally in relation to the second section;
delivering the first section into the aneurysm sac; and
inverting the first section and the second section such that the first section is positioned to occlude the aneurysm neck.

15. The method of claim 14, further comprising:
positioning, after inverting the first section and the second section, the first section to contact an aneurysm wall; and
positioning, after positioning the first section to contact the aneurysm wall, the second section to press the first section to the aneurysm wall.

16. The method of claim 10, further comprising:
connecting a lock positioned proximal to the second section of the implant to a delivery system,
wherein inverting the first section and the second section causes the lock to be disposed distal to the first section.

17. The method of claim 10, wherein, after positioning the first section and the second section, the first section and the second section are contained completely within the aneurysm sac.

18. A method comprising:
delivering, through a catheter, a first portion of an implant into an aneurysm sac, the first portion coated with an anti-thrombogenic coating;
delivering, through the catheter, a second portion of the implant to the aneurysm sac, the second portion coated with a cell adhesion coating; and
inverting the first portion and the second portion such that first portion moves from a position distal to the second portion to a position surrounding at least a portion of the second portion,
wherein the first portion, once inverted, is positioned proximate an aneurysm neck and the second portion is disposed within the aneurysm sac.

19. The method of claim 18, further comprising:
positioning, after inverting the first portion and the second portion, the first portion to contact an aneurysm wall; and
positioning, after positioning the first portion to contact the aneurysm wall, the second portion to press the first portion to the aneurysm wall.

20. The method of claim 18, wherein the second portion is disposed at least partially within the first portion.

* * * * *